US007777048B2

(12) United States Patent
Ansell et al.

(10) Patent No.: US 7,777,048 B2
(45) Date of Patent: Aug. 17, 2010

(54) PROCESSES FOR PREPARING BIARYL UREAS AND ANALOGS THEREOF

(75) Inventors: Graham Ansell, Millbury, MA (US); Todd Blythe, Georgetown, MA (US); Andrew Jones, Needham, MA (US); Benjamin Littler, San Diego, CA (US); Adam Looker, Somerville, MA (US); Philip Nyce, Millbury, MA (US); John Snoonian, Bolton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/435,646

(22) Filed: May 5, 2009

(65) Prior Publication Data

US 2009/0221835 A1    Sep. 3, 2009

Related U.S. Application Data

(62) Division of application No. 11/430,604, filed on May 9, 2006, now Pat. No. 7,544,810.

(60) Provisional application No. 60/679,022, filed on May 9, 2005.

(51) Int. Cl.
    *C07D 413/12*    (2006.01)
(52) U.S. Cl. ..................... 548/236; 549/200

(58) Field of Classification Search .................. None
See application file for complete search history.

(56) References Cited

U.S. PATENT DOCUMENTS

| 5,807,876 | A | 9/1998 | Armistead et al. |
| 6,054,472 | A | 4/2000 | Armistead et al. |
| 6,344,465 | B1 | 2/2002 | Armistead et al. |
| 6,498,178 | B2 | 12/2002 | Stamos et al. |
| 6,541,496 | B1 | 4/2003 | Armistead et al. |
| 6,967,214 | B2 | 11/2005 | Armistead et al. |
| 7,087,642 | B2 | 8/2006 | Stamos et al. |
| 7,329,681 | B2 | 2/2008 | Armistead et al. |
| 2002/0011378 | A1 | 1/2002 | Bailey et al. |
| 2005/0148644 | A1 | 7/2005 | Stamos et al. |

FOREIGN PATENT DOCUMENTS

WO    97/40028    10/1997

OTHER PUBLICATIONS

International Search Report from the counterpart PCT application, 2006.

*Primary Examiner*—Kamal A Saeed
(74) *Attorney, Agent, or Firm*—Michael C. Badia

(57) ABSTRACT

The present invention relates to processes for preparing biaryl ureas derivatives and analogs thereof. The invention also provides compounds useful as intermediates in the processes of the present invention. The process is useful for preparing compounds that inhibit IMPDH.

16 Claims, No Drawings

PROCESSES FOR PREPARING BIARYL UREAS AND ANALOGS THEREOF

CROSS REFERENCE TO RELATED APPLICATIONS

This application is a divisional of U.S. patent application Ser. No. 11/430,604, filed May 9, 2006 now U.S. Pat. No. 7,544,810, which claims the benefit under 35 U.S.C. §119(e) of U.S. provisional application Ser. No. 60/679,022, filed May 9, 2005, the entire contents of each application being incorporated herein by reference.

TECHNICAL FIELD OF THE INVENTION

The present invention relates to processes for preparing biaryl ureas derivatives and analogs thereof. The invention also provides compounds useful as intermediates in the processes of the present invention. The process is useful for preparing compounds that inhibit IMPDH.

BACKGROUND OF THE INVENTION

The present invention provides processes for preparing substituted biaryl ureas and analogs thereof. These compounds are useful for inhibiting IMPDH enzyme activity and consequently, may be advantageously used as therapeutic agents for IMPDH-mediated diseases.

SUMMARY OF THE INVENTION

The present invention provides a process for preparing a compound of formula I:

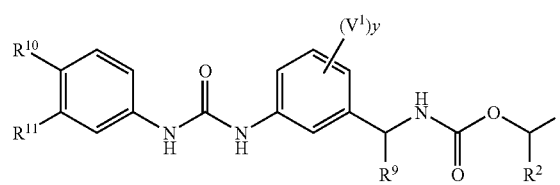

I or a salt thereof, wherein $V^1$, y, $R^1$, $R^2$, $R^9$, $R^{10}$, and $R^{11}$ are as defined below and wherein said process comprises the steps of:

reacting a compound of formula II or a synthetically acceptable analog of derivative thereof with a compound of formula III or a synthetically acceptable analog or derivative thereof, under suitable conditions:

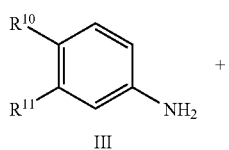

III

-continued

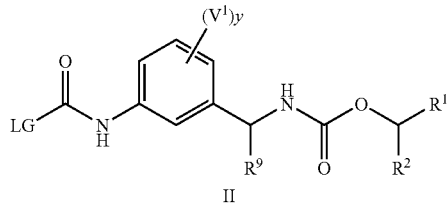

II wherein LG is as defined herein.

The present invention also provides compounds useful as intermediates in the processes of the present invention.

DETAILED DESCRIPTION OF THE INVENTION

According to one embodiment, the present invention provides a process for preparing a compound of formula I:

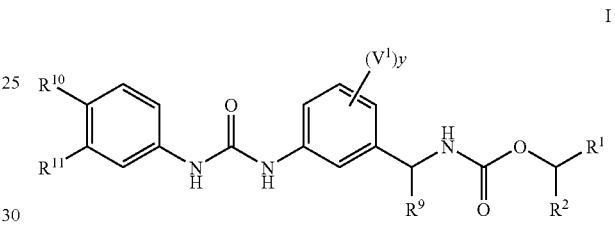

I or a salt thereof, wherein:
y is 0, 1, 2, or 3;
each of $R^1$ and $R^2$ is independently selected from hydrogen; —$CF_3$; —($C_1$-$C_6$)-straight or branched alkyl; —($C_2$-$C_6$)-straight or branched alkenyl or alkynyl; —($C_1$-$C_6$)-straight or branched alkyl-$R^7$; —[($C_2$-$C_6$)-straight or branched alkenyl or alkynyl]-$R^7$ or —$R^7$; and wherein at least one of $R^1$ or $R^2$ is —($C_1$-$C_6$)-straight or branched alkyl-$R^7$; —[($C_2$-$C_6$)-straight or branched alkenyl or alkynyl]-$R^7$ or —$R^7$;
  wherein up to 4 hydrogen atoms in any of said alkyl, alkenyl or alkynyl are optionally and independently replaced by $R^3$; or
$R^1$ and $R^2$ are alternatively taken together to form a tetrahydrofuran ring, wherein up to 2 hydrogen atoms in said tetrahydrofuran ring are optionally replaced by —$OR^6$ or —$R^7$;
each $R_3$ is independently selected from halogen, CN, —$OR^4$, or —$N(R^5)_2$;
$R^4$ is selected from hydrogen, —($C_1$-$C_6$)-straight or branched alkyl, —($C_2$-$C_6$)-straight or branched alkenyl or alkynyl, —[($C_1$-$C_6$)-straight or branched alkyl]-$R^7$, —[($C_2$-$C_6$)-straight or branched alkenyl or alkynyl]-$R^7$, —C(O)—[($C_1$-$C_6$)-straight or branched alkyl], —C(O)—[($C_2$-$C_6$)-straight or branched alkenyl or alkynyl], —C(O)—[($C_1$-$C_6$)-straight or branched alkyl]-$N(R^8)_2$, —C(O)—[($C_2$-$C_6$)-straight or branched alkenyl or alkynyl]-$N(R^8)_2$, —$P(O)(OR^8)_2$, —$P(O)(OR^8)(R^8)$, —C(O)—$R^7$, —$S(O)_2$N($R^5$)$_2$$R^5$—[($C_1$-$C_6$)-straight or branched alkyl]-CN, or —[($C_2$-$C_6$)-straight or branched alkenyl or alkynyl]-CN;
  wherein up to 4 hydrogen atoms in any of said alkyl, alkenyl or alkynyl are optionally and independently replaced by —C=O or Y;
Y is selected from halogen, CN, $NO_2$, $CF_3$, $OCF_3$, $SR^8$, $S(O)R^8$, $SO_2R^8$, $NHR^8$, $N(R^8)_2$, $COOR^8$ or $OR^8$;

each $R^5$ is independently selected from hydrogen, $-(C_1-C_6)$-straight or branched alkyl, $-(C_2-C_6)$-straight or branched alkenyl or alkynyl, $-[(C_1-C_6)$-straight or branched alkyl]-$R^7$, $-[(C_2-C_6)$-straight or branched alkenyl or alkynyl]-$R^7$, $-[(C_1-C_6)$-straight alkyl]-CN, $-[(C_2-C_6)$-straight or branched alkenyl or alkynyl]-CN, $-[(C_1-C_6)$-straight or branched alkyl]-$OR^4$, $-[(C_2-C_6)$-straight or branched alkenyl or alkynyl]-$OR^4$, $-C(O)-(C_1-C_6)$-straight or branched alkyl, $-C(O)-[(C_2-C_6)$-straight or branched alkenyl or alkynyl], $-C(O)-R^7$, $-C(O)O-R^7$, $-C(O)O-(C_1-C_6)$-straight or branched alkyl, $-C(O)O-[(C_2-C_6)$-straight or branched alkenyl or alkynyl], $-S(O)_2-(C_1-C_6)$-straight or branched alkyl, or $-S(O)_2-R^7$; or two $R^5$ moieties, when bound to the same nitrogen atom, are taken together with said nitrogen atom to form a 3 to 7-membered heterocyclic ring, wherein said heterocyclic ring optionally contains 1 to 3 additional heteroatoms independently selected from N, O, S, S(O) or $S(O)_2$;
  wherein up to 4 hydrogen atoms in any of said alkyl, alkenyl or alkynyl are optionally and independently replaced by $-C=O$ or Y;
$R^6$ is selected from $-C(O)-CH_3$, $-CH_2-C(O)-OH$, $-CH_2-C(O)-O$-tBu, $-CH_2-CN$, or $-CH_2-C\equiv CH$;
each $R_7$ is a monocyclic or bicyclic ring system wherein in said ring system:
  i. each ring comprises 3 to 7 ring atoms independently selected from C, N, O or S;
  ii. no more than 4 ring atoms are selected from N, O or S;
  iii. any $CH_2$ is optionally replaced with C(O);
  iv. any S is optionally replaced with S(O) or $S(O)_2$;
  v. up to 3 hydrogen atoms in said monocyclic ring system or up to 6 hydrogens in said bicyclic ring system are optionally replaced by $V^1$;
each $R^8$ is independently selected from hydrogen, $-(C_1-C_4)$-straight or branched alkyl, or $-(C_2-C_4)$-straight or branched alkenyl;
  wherein up to 4 hydrogen atoms in any of said alkyl or alkenyl are optionally and independently replaced by halogen, CN, $NO_2$, $CF_3$, $OCF_3$, $SR^{17}$, $S(O)R^{17}$, $SO_2R^{17}$, $NHR^{17}$, $N(R^{17})_2$, $COOR^{17}$ or $OR^{17}$;
    wherein $R^{17}$ is selected from hydrogen, $-(C_1-C_6)$-straight or branched alkyl, $-(C_2-C_6)$-straight or branched alkenyl or alkynyl;
$R^9$ is selected from hydrogen, or $-(C_1-C_6)$-straight or branched alkyl or $(C_3-C_6)$-cycloaliphatic;
  wherein up to 4 hydrogen atoms in any of said alkyl, or cycloaliphatic are optionally and independently replaced by $-C=O$ or Y;
$R^{10}$ is selected from $R^8$, $(CH_2)_n-Y$, or a monocyclic ring system wherein in said ring system:
  i. the ring comprises 5 to 7 ring atoms independently selected from C, N, O or S;
  ii. no more than 4 ring atoms are selected from N, O or S;
  iii. any $CH_2$ is optionally replaced with C(O);
  iv. any S is optionally replaced with S(O) or $S(O)_2$; and
  v. up to 3 hydrogen atoms in said monocyclic ring system are optionally replaced by $V^1$;
n is 0, 1, 2, 3, or 4;
$R^{11}$ is selected from $R^8$ or $(CH_2)_n-Y$;
each $V^1$ is independently selected from halogen, $NO_2$, CN, $OR^{12}$, $OC(O)R^{13}$, $OC(O)R^{12}$, $C(O)OR^{13}$, $OC(O)OR^{12}$, $OC(O)N(R^{13})_2$, $OP(O)(OR^{13})_2$, $SR^{13}$, $SR^{12}$, $S(O)R^{13}$, $S(O)R^{12}$, $SO_2R^{13}$, $SO_2R^{12}$, $SO_2N(R^{13})_2$, $SO_2NR^{12}R^{13}$, $SO_3R^{13}$, $C(O)R^{12}$, $C(O)OR^{12}$, $C(O)R^{13}$, $C(O)OR^{13}$, $NC(O)C(O)R^{13}$, $NC(O)C(O)R^{12}$, $NC(O)C(O)OR^{13}$, $NC(O)C(O)N(R^{13})_2$, $C(O)N(R^{13})_2$, $C(O)N(OR^{13})R^{13}$, $C(O)N(OR^{13})R^{12}$, $C(NOR^{13})R^{13}$, $C(NOR^{13})R^{12}$, $N(R^{13})_2$, $NR^{13}C(O)R^2$, $NR^{13}C(O)R^3$, $NR^{12}C(O)R^{13}$, $NR^{13}C(O)OR^{13}$, $NR^{13}C(O)OR^{12}$, $NR^{13}C(O)N(R^{13})_2$, $NR^{13}C(O)R^{12}$, $NR^{13}SO_2R^{13}$, $NR^{13}SO_2R^{12}$, $NR^{13}SO_2N(R^{13})_2$, $NR^{13}SO_2NR^{13}R^{13}$, $N(OR^{13})R^{13}$, $N(OR^{13})R^{12}$, $P(O)(OR^{13}))N(R^{13})_2$, and $P(O)(OR^{13})_2$;
wherein each $R^{12}$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S may be substituted with C(O); and each $R^{12}$ optionally comprises up to 3 substituents selected from $R^{11}$;
wherein each $R^{13}$ is independently selected from H, $(C_1-C_4)$-straight or branched alkyl, or $(C_2-C_4)$ straight or branched alkenyl; and
wherein each $R^{13}$ optionally comprises a substituent that is $R^{14}$;
  wherein $R^{14}$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S maybe substituted with C(O); and each $R^{14}$ optionally comprises up to 2 substituents independently chosen from H, $(C_1-C_4)$-straight or branched alkyl, or $(C_2-C_4)$ straight or branched alkenyl, 1,2-methylenedioxy, 1,2-ethylenedioxy, or $(CH_2)_n-Z$;
    wherein Z is selected from halogen, CN, $NO_2$, $CF_3$, $OCF_3$, OH, $S(C_1-C_4)$-alkyl, $SO(C_1-C_4)$-alkyl, $SO_2(C_1-C_4)$-alkyl, $NH_2$, $NH(C_1-C_4)$-alkyl, $N((C_1-C_4)$-alkyl$)_2$, COOH, $C(O)O(C_1-C_4)$-alkyl or $O(C_1-C_4)$-alkyl; and
wherein any carbon atom in any $R^{13}$ is optionally replaced by O, S, SO, $SO_2$, NH, or $N(C_1-C_4)$-alkyl;
said process comprising the step of:
reacting a compound of formula II or a synthetically acceptable analog or derivative thereof with a compound of formula III or a synthetically acceptable analog or derivative thereof, under suitable conditions:

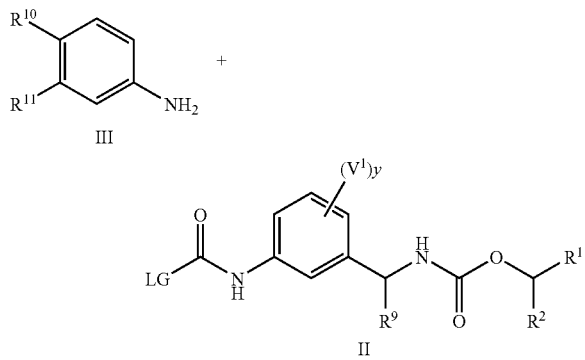

wherein:
LG is $-OR^{16}$; wherein $R^{16}$ is $-(C_1-C_6)$-straight or branched alkyl; $-(C_2-C_6)$-straight or branched alkenyl or alkynyl; or a monocyclic ring system consisting of 5 to 6 members per ring, wherein said ring system optionally comprises up to 3 heteroatoms selected from N, O, or S, and each $R^{16}$ optionally comprises up to 5 substituents independently selected from $(C_1-C_4)$-straight or branched alkyl, $(C_2-C_4)$ straight or branched alkenyl, or $(CH_2)_n$—Z;

$V^1$, y, n, Z, $R^1$, $R^2$, $R^9$, $R^{10}$, $R^{11}$, and $R^{15}$, are as defined above; and provided that $R^{16}$ is not a halo-substituted $(C_2-C_3)$-straight alkyl.

In another embodiment, the present invention provides a process for preparing a compound of formula I:

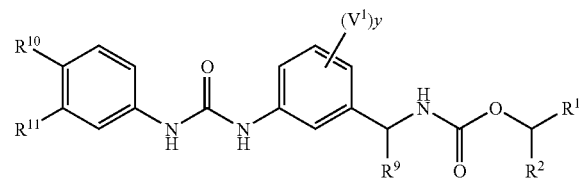

I or a salt thereof, wherein:

y is 0, 1, 2, or 3;

each of $R^1$ and $R^2$ is independently selected from hydrogen; —$CF_3$; —$(C_1-C_6)$-straight or branched alkyl; —$(C_2-C_6)$-straight or branched alkenyl or alkynyl; —$(C_1-C_6)$-straight or branched alkyl-$R^7$; —[$(C_2-C_6)$-straight or branched alkenyl or alkynyl]-$R^7$ or —$R^7$; and wherein at least one of $R^1$ or $R^2$ is —$(C_1-C_6)$-straight or branched alkyl-$R^7$; —[$(C_2-C_6)$-straight or branched alkenyl or alkynyl]-$R^7$ or —$R^7$;

wherein up to 4 hydrogen atoms in any of said alkyl, alkenyl or alkynyl are optionally and independently replaced by $R^3$; or $R^1$ and $R^2$ are alternatively taken together to form a tetrahydrofuran ring, wherein up to 2 hydrogen atoms in said tetrahydrofuran ring are optionally replaced by —$OR^6$ or —$R^7$;

each $R_3$ is independently selected from halogen, CN, —$OR^4$, or —$N(R^5)_2$;

$R^4$ is selected from hydrogen, —$(C_1-C_6)$-straight or branched alkyl, —$(C_2-C_6)$-straight or branched alkenyl or alkynyl, —[$(C_1-C_6)$-straight or branched alkyl]-$R^7$, —[$(C_2-C_6)$-straight or branched alkenyl or alkynyl]-$R^7$, —C(O)—[$(C_1-C_6)$-straight or branched alkyl], —C(O)—[$(C_2-C_6)$-straight or branched alkenyl or alkynyl], —C(O)—[$(C_1-C_6)$-straight or branched alkyl]-$N(R^3)_2$, —C(O)—[$(C_2-C_6)$-straight or branched alkenyl or alkynyl]-$N(R^8)_2$, —P(O)(OR^8)_2, —P(O)(OR^8)(R^8), —C(O)—$R^7$, —$S(O)_2N(R^5)_2$, —[$(C_1-C_6)$-straight or branched alkyl]-CN, or —[$(C_2-C_6)$-straight or branched alkenyl or alkynyl]-CN;

wherein up to 4 hydrogen atoms in any of said alkyl, alkenyl or alkynyl are optionally and independently replaced by —C=O or Y;

Y is selected from halogen, CN, $NO_2$, $CF_3$, $OCF_3$, $SR^8$, $S(O)R^8$, $SO_2R^8$, $NHR^8$, $N(R^8)_2$, $COOR^8$ or $OR^8$;

each $R^5$ is independently selected from hydrogen, —$(C_1-C_6)$-straight or branched alkyl, —$(C_2-C_6)$-straight or branched alkenyl or alkynyl, —[$(C_1-C_6)$-straight or branched alkyl]-$R^7$, —[$(C_2-C_6)$-straight or branched alkenyl or alkynyl]-$R^7$, —[$(C_1-C_6)$-straight alkyl]-CN, —[$(C_2-C_6)$-straight or branched alkenyl or alkynyl]-CN, —[$(C_1-C_6)$-straight or branched alkyl]-$OR^4$-[$(C_2-C_6)$-straight or branched alkenyl or alkynyl]-$OR^4$, —C(O)—$(C_1-C_6)$-straight or branched alkyl, —C(O)—[$(C_2-C_6)$-straight or branched alkenyl or alkynyl], —C(O)—$R^7$, —C(O)O—$R^7$, —C(O)O—$(C_1-C_6)$-straight or branched alkyl, —C(O)O—[$(C_2-C_6)$-straight or branched alkenyl or alkynyl], —$S(O)_2$—$(C_1-C_6)$-straight or branched alkyl, or —$S(O)_2$—$R^7$; or two $R^5$ moieties, when bound to the same nitrogen atom, are taken together with said nitrogen atom to form a 3 to 7-membered heterocyclic ring, wherein said heterocyclic ring optionally contains 1 to 3 additional heteroatoms independently selected from N, O, S, S(O) or $S(O)_2$;

wherein up to 4 hydrogen atoms in any of said alkyl, alkenyl or alkynyl are optionally and independently replaced by —C=O or Y;

$R^6$ is selected from —$C(O)$—$CH_3$, —$CH_2$—$C(O)$—OH, —$CH_2$—$C(O)$—O-tBu, —$CH_2$—CN, or —$CH_2$—C≡CH;

each $R_7$ is a monocyclic or bicyclic ring system wherein in said ring system:

i. each ring comprises 3 to 7 ring atoms independently selected from C, N, O or S;

ii. no more than 4 ring atoms are selected from N, O or S;

iii. any $CH_2$ is optionally replaced with C(O);

iv. any S is optionally replaced with S(O) or $S(O)_2$;

v. up to 3 hydrogen atoms in said monocyclic ring system or up to 6 hydrogens in said bicyclic ring system are optionally replaced by $V^1$;

each $R^8$ is independently selected from hydrogen, —$(C_1-C_4)$-straight or branched alkyl, or —$(C_2-C_4)$-straight or branched alkenyl;

wherein up to 4 hydrogen atoms in any of said alkyl or alkenyl are optionally and independently replaced by halogen, CN, $NO_2$, $CF_3$, $OCF_3$, $SR^{17}$, $S(O)R^{17}$, $SO_2R^{17}$, $NHR^{17}$, $N(R^{17})_2$, $COOR^{17}$ or $OR^{17}$;

wherein $R^{17}$ is selected from hydrogen, —$(C_1-C_6)$-straight or branched alkyl, —$(C_2-C_6)$-straight or branched alkenyl or alkynyl;

$R^9$ is selected from hydrogen, or —$(C_1-C_6)$-straight or branched alkyl or $(C_3-C_6)$-cycloaliphatic;

wherein up to 4 hydrogen atoms in any of said alkyl, or cycloaliphatic are optionally and independently replaced by —C=O or Y;

$R^{10}$ is selected from $R^8$, $(CH_2)_n$—Y, or a monocyclic ring system wherein in said ring system:

i. the ring comprises 5 to 7 ring atoms independently selected from C, N, O or S;

ii. no more than 4 ring atoms are selected from N, O or S;

iii. any $CH_2$ is optionally replaced with C(O);

iv. any S is optionally replaced with S(O) or $S(O)_2$; and v. up to 3 hydrogen atoms in said monocyclic ring system are optionally replaced by $V^1$;

n is 0, 1, 2, 3, or 4;

$R^{11}$ is selected from $R^3$ or $(CH_2)_n$—Y;

each $V^1$ is independently selected from halogen, $NO_2$, CN, $OR^{12}$, $OC(O)R^{13}$, $OC(O)R^{12}$, $OC(O)OR^{13}$, $OC(O)OR^{12}$, $OC(O)N(R^{13})_2$, $OP(O)(OR^{13})_2$, $SR^{13}$, $SR^{12}$, $S(O)R^{13}$, $S(O)R^{13}$, $SO_2R^{12}$, $SO_2R^{12}$, $SO_2N(R^{13})_2$, $SO_2NR^{12}R^{13}$, $SO_3R^{13}$, $C(O)R^{12}$, $C(O)OR^{12}$, $C(O)R^{13}$, $C(O)OR^{13}$, $NC(O)C(O)R^{13}$, $NC(O)C(O)R^{12}$, $NC(O)C(O)OR^{13}$, $NC(O)C(O)N(R^{13})_2$, $C(O)N(R^{13})_2$, $C(O)N(OR^{13})R^{13}$, $C(O)N(OR^{13})R^{12}$, $C(NOR^{13})R^{13}$, $C(NOR^{13})R^{12}$, $N(R^{13})_2$, $NR^{13}C(O)R^{12}$, $NR^{13}C(O)R^{13}$, $NR^{13}C(O)R^{12}$, $NR^{13}C(O)OR^{13}$, $NR^{13}C(O)OR^{12}$, $NR^{13}C(O)N(R^3)_2$, $NR^{13}C(N^{12}R^{13}$, $NR^{13}SO_2R^{13}$, $NR^{13}SO_2R^{12}$, $NR^{13}SO_2N(R^{13})_2$, $NR^{13}SO_2NR^{12}R^{13}$, $N(OR^{13})R^{13}$, $N(OR^{13})R^{12}$, $P(O)(OR^{13})N(R^{13})_2$, and $P(O)(OR^{13})_2$;

wherein each $R^{12}$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S may be substituted with C(O); and each $R^{12}$ optionally comprises up to 3 substituents selected from $R^{11}$;

wherein each $R^{13}$ is independently selected from H, $(C_1-C_4)$-straight or branched alkyl, or $(C_2-C_4)$ straight or branched alkenyl; and wherein each $R^{13}$ optionally comprises a substituent that is $R^{14}$;

wherein $R^{14}$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S maybe substituted with C(O); and each $R^{14}$ optionally comprises up to 2 substituents independently chosen from H, $(C_1-C_4)$-straight or branched alkyl, or $(C_2-C_4)$ straight or branched alkenyl, 1,2-methylenedioxy, 1,2-ethylenedioxy, or $(CH_2)_n$—Z;

wherein Z is selected from halogen, CN, $NO_2$, $CF_3$, $OCF_3$, OH, $S(C_1-C_4)$-alkyl, $SO(C_1-C_4)$-alkyl, $SO_2(C_1-C_4)$-alkyl, $NH_2$, $NH(C_1-C_4)$-alkyl, $N((C_1-C_4)$-alkyl$)_2$, COOH, $C(O)O(C_1-C_4)$-alkyl or $O(C_1-C_4)$-alkyl; and wherein any carbon atom in any $R^{13}$ is optionally replaced by O, S, SO, $SO_2$, NH, or $N(C_1-C_4)$-alkyl;

said process comprising the step of:
reacting a compound of formula II or a synthetically acceptable analog or derivative thereof with a compound of formula III or a synthetically acceptable analog or derivative thereof, under suitable conditions:

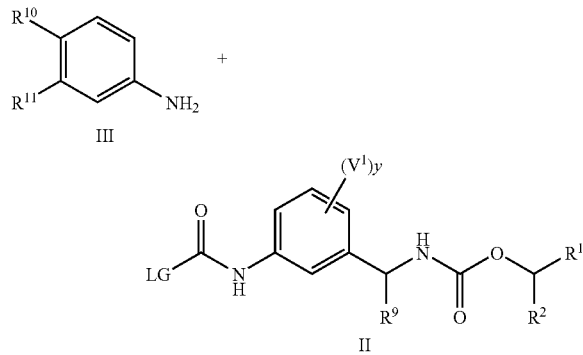

wherein:
LG is —$OR^{16}$; wherein $R^{16}$ is —$(C_1-C_6)$-straight or branched alkyl; —$(C_2-C_6)$-straight or branched alkenyl or alkynyl; or a monocyclic ring system consisting of 5 to 6 members per ring, wherein said ring system optionally comprises up to 3 heteroatoms selected from N, O, or S, and each $R^{16}$ optionally comprises up to 5 substituents independently selected from $(C_1-C_4)$-straight or branched alkyl, $(C_2-C_4)$ straight or branched alkenyl, or $(CH_2)_n$—Z; and $V^1$, y, n, Z, $R^1$, $R^2$, $R^9$, $R^{10}$, $R^{11}$, and $R^{15}$ are as defined above.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As used herein the term "suitable conditions" means reaction conditions such as solvent, temperature, time of reaction, etc. Such suitable conditions are readily known to one of skill in the art and vary depending on the particular compound desired.

As used herein the term "suitable phosgene reagent equivalent" includes, but is not limited to, diphosgene, triphosgene, and other suitable reagents known to one of skill in the art.

As used herein the term "amino protecting group" means a group that is known to be an amino protecting group in the art. See, e.g. "Protective Groups in Organic Synthesis," Greene, J. W. et al., 3rd Ed., John Wiley & Sons, 1999, the contents of which are incorporated herein by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle", "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3-C_8$ hydrocarbon or bicyclic $C_8-C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" or "halo" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

Examples of monocyclic and bicyclic ring systems useful in the compounds of this invention include, but are not limited to, cyclopentane, cyclopentene, indane, indene, cyclohexane, cyclohexene, cyclohexadiene, benzene, tetrahydronaphthalene, decahydronaphthalene, naphthalene, pyridine, piperidine, pyridazine, pyrimidine, pyrazine, 1,2,3-triazine, 1,2,4-triazine, 1,3,5-triazine, 1,2,3,4-tetrazine, 1,2,4,5-tetrazine, 1,2,3,4-tetrahydroquinoline, quinoline, 1,2,3,4-tetrahydroisoquinoline, isoquinoline, cinnoline, phthalazine, quinazoline, quinoxaline, 1,5-naphthyridine, 1,6-naphthyridine, 1,7-naphthyridine, 1,8-naphthyridine, 2,6-naphthyridine, 2,7-naphthyridine, pteridine, acridine, phenazine, 1,10-phenatroline, dibenzopyrans, 1-benzopyrans, phenothiazine, phenoxazine, thianthrene, dibenzo-p-dioxin, phenoxathiin, phenoxthionine, morpholine, thiomorpholine, tetrahydropyan, pyran, benzopyran, 1,4-dioxane, 1,3-dioxane, dihydropyridine, dihydropyran, 1-pyrindine, quinuclidine, triazolopyridine, β-carboline, indolizine, quinolizidine, tetrahydronaphtheridine, diazaphenanthrenes, thiopyran, tetrahydrothiopyran, benzodioxane, furan, benzofuran, tetrahydrofuran, pyrrole, indole, thiophene, benzothiopene, carbazole, pyrrolidine, pyrazole, isoxazole, isothiazole, imidazole, oxazole, thiazole, 1,2,3-triazole, 1,2,4-triazole, 1,2,3-oxadiazole, 1,2,4-oxadiazole, 1,3,4-oxadiazole, 1,2,5-oxadiazole, 1,2,3-thiadiazole, 1,2,4-thiadiazole, 1,3,4-thiadiazole, 1,2,5-thiadiazole, tetrazole, benzothiazole, benzoxazole, benzotriazole, benzimidazole, benzopyrazole, benzisothiazole, benzisoxazole and purine.

Additional monocyclic and bicyclic structures falling within the above description may be found in A. R. Katritzky, and C. W. Rees, eds. "Comprehensive Heterocyclic Chemistry: Structure, Reactions, Synthesis and Use of Heterocyclic Compounds, Vol. 1-8," Pergamon Press, NY (1984), the disclosure of which is herein incorporated by reference.

An aryl (including aralkyl, aralkoxy, aryloxyalkyl and the like) or heteroaryl (including heteroaralkyl and heteroarylalkoxy and the like) group may contain one or more substituents. Unless specified otherwise, suitable substituents on the unsaturated carbon atom of an aryl or heteroaryl group are selected from halogen; —R$^\circ$; —OR$^\circ$; —SR$^\circ$; 1,2-methylenedioxy; 1,2-ethylenedioxy; phenyl (Ph) optionally substituted with R$^\circ$; —O(Ph) optionally substituted with R$^\circ$; —(CH$_2$)$_{1-2}$(Ph), optionally substituted with R$^\circ$; —CH=CH(Ph), optionally substituted with R$^\circ$; —NO$_2$; —CN; —N(R$^\circ$)$_2$; —NR$^\circ$C(O)R$^\circ$; —NR$^\circ$C(S)R$^\circ$; —NR$^\circ$C(O)N(R$^\circ$)$_2$; —NR$^\circ$C(S)N(R$^\circ$)$_2$; —NR$^\circ$CO$_2$R$^\circ$; —NR$^\circ$NR$^\circ$C(O)R$^\circ$; —NR$^\circ$NR$^\circ$C(O)N(R$^\circ$)$_2$; —NR$^\circ$NR$^\circ$CO$_2$R$^\circ$; —C(O)C(O)R$^\circ$; —C(O)CH$_2$C(O)R$^\circ$; —CO$_2$R$^\circ$; —C(O)R$^\circ$; —C(S)R$^\circ$; —C(O)N(R$^\circ$)$_2$; —C(S)N(R$^\circ$)$_2$; —OC(O)N(R$^\circ$)$_2$; —OC(O)R$^\circ$; —C(O)N(OR$^\circ$) R$^\circ$; —C(NOR$^\circ$)R$^\circ$; —OP(O)(OR$^\circ$)$_2$, —P(O)(OR$^\circ$)$_2$, —P(O)(OR$^\circ$)R$^\circ$, —S(O)$_2$R$^\circ$; —S(O)$_3$R$^\circ$; —SO$_2$N(R$^\circ$)$_2$; —S(O)R$^\circ$; —NR$^\circ$SO$_2$N(R$^\circ$)$_2$; —NR$^\circ$SO$_2$R$^\circ$; —N(OR$^\circ$)R$^\circ$; —C(=NH)—N(R$^\circ$)$_2$; or —(CH$_2$)$_{0-2}$NHC(O)R$^\circ$ wherein each independent occurrence of R$^\circ$ is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R$^\circ$, on the same substituent or different substituents, taken together with the atom(s) to which each R$^\circ$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of R$^\circ$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O-halo(C$_{1-4}$ aliphatic), or halo(C$_{1-4}$ aliphatic), wherein each of the foregoing C$_{1-4}$ aliphatic groups of R$^\circ$ is unsubstituted.

An aliphatic or heteroaliphatic group, or a non-aromatic heterocyclic ring may contain one or more substituents. Unless specified otherwise, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O-halo($C_{1-4}$ aliphatic), or halo($C_{1-4}$ aliphatic), wherein each of the foregoing $C_{1-4}$ aliphatic groups of R* is unsubstituted.

Unless specified otherwise, optional substituents on the nitrogen of a non-aromatic heterocyclic ring are selected from $-R^+$, $-N(R^+)_2$, $-C(O)R^+$, $-CO_2R^+$, $-C(O)C(O)R^+$, $-C(O)CH_2C(O)R^+$, $-SO_2R^+$, $-SO_2N(R^+)_2$, $-C(=S)N(R^+)_2$, $-C(=NH)-N(R^+)_2$, or $-NR^+SO_2R^+$; wherein $R^+$ is hydrogen, an optionally substituted $C_{1-6}$ aliphatic, optionally substituted phenyl, optionally substituted $-O(Ph)$, optionally substituted $-CH_2(Ph)$, optionally substituted $-(CH_2)_{1-2}(Ph)$; optionally substituted $-CH=CH(Ph)$; or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of $R^+$ are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$ aliphatic groups of $R^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of $R^o$ (or $R^+$, or any other variable similarly defined herein), are taken together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of $R^o$ (or $R^+$, or any other variable similarly defined herein) are taken together with the atom(s) to which each variable is bound include, but are not limited to the following: a) two independent occurrences of $R^o$ (or $R^+$, or any other variable similarly defined herein) that are bound to the same atom and are taken together with that atom to form a ring, for example, $N(R^o)_2$, where both occurrences of $R^o$ are taken together with the nitrogen atom to form a piperidin-1-yl, piperazin-1-yl, or morpholin-4-yl group; and b) two independent occurrences of $R^o$ (or $R^+$, or any other variable similarly defined herein) that are bound to different atoms and are taken together with both of those atoms to form a ring, for example where a phenyl group is substituted with two occurrences of $OR^o$

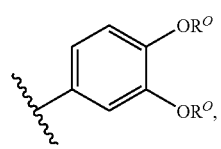

these two occurrences of $R^o$ are taken together with the oxygen atoms to which they are bound to form a fused 6-membered oxygen containing ring:

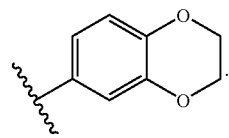

It will be appreciated that a variety of other rings can be formed when two independent occurrences of $R^o$ (or $R^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

According to one embodiment, the present invention provides novel processes to prepare biaryl urea compounds useful as IMPDH inhibitors such as those disclosed in U.S. Pat. Nos. 5,807,876, 6,054,472, 6,344,465, 6,541,496, and 6,498,178.

According to another embodiment, the present invention provides a process shown in Scheme 1 below:

Scheme 1:

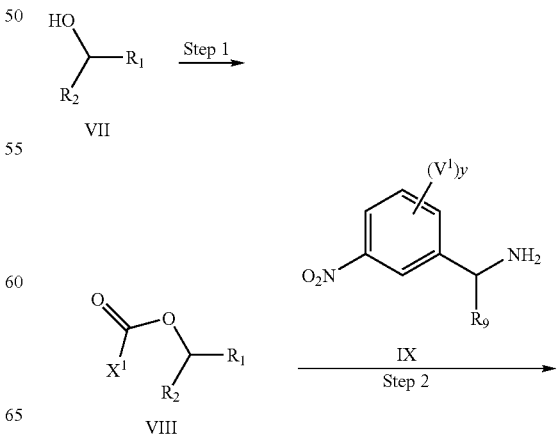

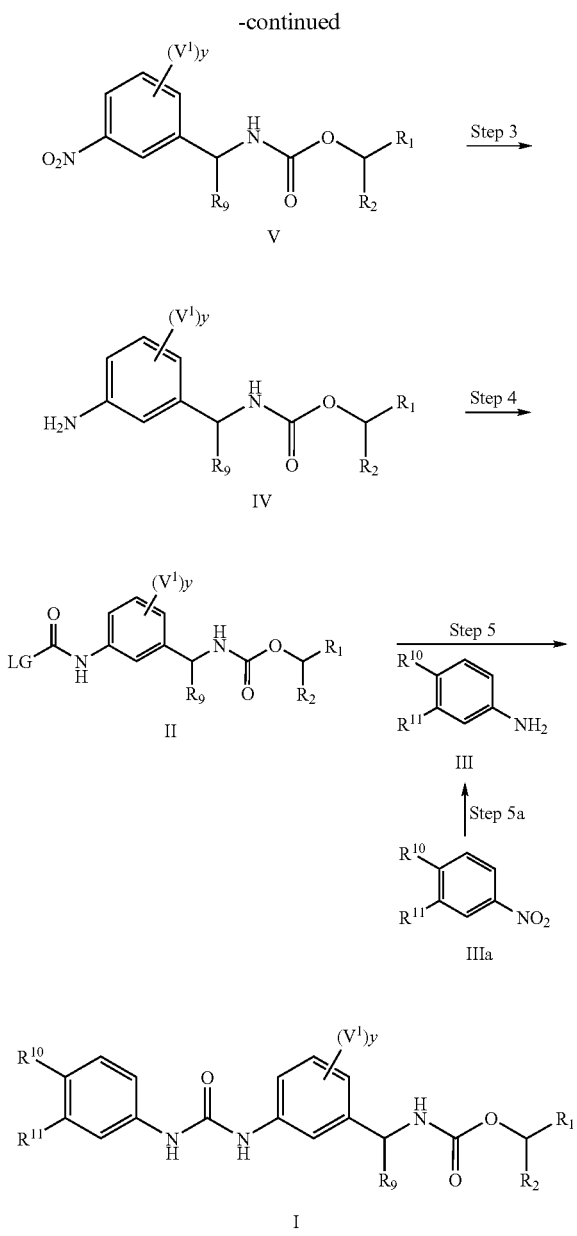

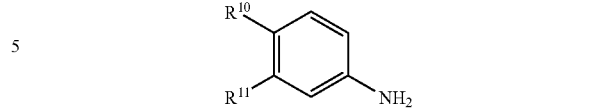

or a salt thereof.

According to another embodiment for the process for producing a compound of formula III, said suitable catalytic hydrogenation conditions comprise one or more of the following: a suitable metal catalyst; a suitable solvent selected from a protic solvent, a polar aprotic solvent, a non-polar aprotic solvent or any mixtures thereof; a suitable reaction atmosphere of hydrogen gas at a suitable pressure; and a suitable reaction temperature.

According to another embodiment for the process for producing a compound of formula III, said metal catalyst is between about 1% to about 30% by weight palladium metal on carbon; said protic solvent is selected from a $(C_1-C_5)$-straight or branched alkyl alcohol; said aprotic solvent is selected from an ester-type solvent; said reaction atmosphere comprises hydrogen gas at between about one to about ten atmospheres of pressure; and said reaction temperature is between about 20° C. to about 60° C.

According to another embodiment for the process for producing a compound of formula III, said metal catalyst is between about 5% to about 10% by weight palladium metal on carbon; said protic solvent is selected from methanol, ethanol, or isopropanol; said aprotic solvent is selected from ethyl acetate or isopropyl acetate; said reaction atmosphere of hydrogen gas is between about one to about eight atmospheres of pressure; and said reaction temperature is between about 30° C. to about 50° C.

According to another embodiment for the process for producing a compound of formula III, said metal catalyst is between about 5% to about 10% by weight palladium metal on carbon; said protic solvent is selected from methanol, ethanol, or isopropanol; said aprotic solvent is selected from ethyl acetate or isopropyl acetate; said reaction atmosphere of hydrogen gas is between about one to about eight atmospheres of pressure; and said reaction temperature is between about 30° C. to about 50° C.

According to another embodiment for the process for producing a compound of formula III, said metal catalyst is about 5% by weight palladium metal on carbon; said aprotic solvent is isopropyl acetate; said reaction atmosphere of hydrogen gas is about four atmospheres of pressure; and said reaction temperature is between about 35° C. to about 45° C.

According to another embodiment for the process for producing a compound of formula III, said metal catalyst is between about 1% to about 5% by weight platinum metal plus between about 1% to about 5% by weight vanadium metal on carbon; no protic solvent is used, said aprotic solvent is selected from an ester-type solvent; said reaction atmosphere comprises hydrogen gas at between about one to about ten atmospheres of pressure; and said reaction temperature is between about 20° C. to about 70° C.

According to another embodiment for the process for producing a compound of formula III, said metal catalyst is between about 1% to about 2% by weight platinum metal plus between about 1% to about 3% by weight vanadium metal on carbon; no protic solvent is used, said aprotic solvent is ethyl acetate; said reaction atmosphere comprises hydrogen gas at Step 5a Embodiments According to one embodiment for the process for producing a compound of formula III from compound IIIa; compound IIIa,

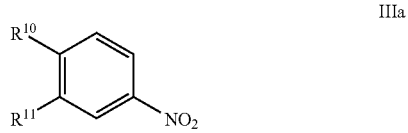

is reacted under suitable catalytic hydrogenation conditions to give a compound of formula III:

between about one to about two atmospheres of pressure; and said reaction temperature is between about 50° C. to about 65° C.

Step 5 Embodiments

According to one embodiment for the process for producing a compound of formula I, the suitable conditions comprise a suitable polar or nonpolar aprotic, substantially anhydrous solvent or mixtures thereof.

According to another embodiment for the process for producing a compound of formula I, the solvent is selected from ethyl acetate, isopropyl acetate, n-butyl acetate, acetonitrile, chloroform, dichloromethane, dichloroethane, dimethylformamide (DMF), 1-methyl-2-pyrrolidinone (NMP), N,N,-dimethylacetamide (DMAC), methyl sulfoxide (DMSO), acetone, methyl ethyl ketone or 2-butanone (MEK), methyl isobutyl ketone or 4-methyl-2-pentanone (MIBK), tetrahydrofuran, 2-methyltetrahydrofuran, acetone, toluene, trifluorotoluene, benzene, chlorobenzene, or dichlorobenzene.

According to another embodiment for the process for producing a compound of formula I, the solvent is selected from ethyl acetate, isopropyl acetate, n-butyl acetate, or acetonitrile. In yet another embodiment, the solvent is ethyl acetate.

According to another embodiment for the process for producing a compound of formula I, the suitable conditions comprise a suitable base selected from an organic base, an inorganic base, or a suitable combination of an organic base and an inorganic base.

According to another embodiment for the process for producing a compound of formula I, the organic base is selected from diisopropylethylamine, triethylamine, tributylamine, pyridine, collidine, 2,6-lutidine, methylpyridine, 4-dimethylaminopyridine, N-methylpyrrolidine, N-methylmorpholine, 1-methylimidazole, 1,8-diazabicyclo[5.4.0]undec-7-ene, 2,2,6,6-tetramethylpiperidine, or 1,1,3,3-tetramethylguanidine.

According to another embodiment for the process for producing a compound of formula I, the organic base is selected from diisopropylethylamine, triethylamine, or 4-dimethylaminopyridine. In yet another embodiment, the organic base is diisopropylethylamine.

According to another embodiment for the process for producing a compound of formula I, the inorganic base is selected from is selected from $Na_2CO_3$, $K_2CO_3$, $Cs_2CO_3$, $Li_2CO_3$, $NaHCO_3$, or $KHCO_3$.

According to another embodiment for the process for producing a compound of formula I, the suitable conditions do not include an organic or inorganic base. In yet another embodiment for the process for producing a compound of formula I, the suitable conditions comprise 1-methyl-2-pyrrolidinone as solvent, a temperature of about 100° C. and no added organic or inorganic base.

According to another embodiment for the process for producing a compound of formula I, the suitable conditions comprise heating the reaction mixture from about 30° C. to about 180° C. for about one hour to about forty eight hours in a substantially inert atmosphere.

According to another embodiment for the process for producing a compound of formula I, the reaction mixture is heated from about 50° C. to about 100° C. for about five hours to about 30 hours in a substantially inert atmosphere. In yet another embodiment, the reaction mixture is heated at about 70° C. to about 80° C. for about 20-30 hours under a nitrogen atmosphere. In another embodiment, the reaction mixture contains ethyl acetate as solvent and the reaction mixture is refluxed for 24 hours under a nitrogen atmosphere.

According to another embodiment for the process for producing a compound of formula I, the reaction mixture is heated from about 50° C. to about 100° C. for about five hours to about 30 hours in a substantially inert atmosphere. In yet another embodiment, the reaction mixture is heated at about 70° C. to about 80° C. for about 20-30 hours under a nitrogen atmosphere.

In another embodiment, the reaction mixture contains ethyl acetate as solvent and the reaction mixture is refluxed for 24 hours under a nitrogen atmosphere.

According to another embodiment for the process for producing a compound of formula I, the reaction mixture contains ethyl acetate as solvent, diisopropylamine as organic base and the reaction mixture is refluxed at 75-85° C. for 24-32 hours under a nitrogen atmosphere.

According to another embodiment for the process for producing a compound of formula I, the process comprises one or more of the following steps:

(i) purifying said compound of formula I by heating said compound in a suitable mixture of suitable solvents from about 30° C. to about 100° C.; then cooling said mixture;

(ii) filtering precipitated solid from said mixture;

(iii) rinsing said solid with a suitable solvent; and (iv) drying said compound of formula I, in vacuo, from about room temperature to about 100° C.

According to another embodiment for the process for producing a compound of formula I, the process comprises one or more of the following steps:

(i) said compound of formula I is heated in a suitable mixture comprising a polar aprotic solvent and a polar protic solvent from about 40° C. to about 80° C.; said mixture is cooled to about room temperature;

(ii) filtering precipitated solid from said mixture;

(iii) said precipitated solid is rinsed with a polar protic solvent; and (iv) said compound is dried, in vacuo, from about 30° C. to about 80° C.

According to another embodiment for the process for producing a compound of formula I, the process comprises the following steps:

(i) said compound of formula I is heated in a mixture of 1-methyl-2-pyrrolidinone and methanol from about 40° C. to about 60° C.; said mixture is cooled to about 0° C., then to about room temperature;

(ii) filtering precipitated solid from said mixture;

(iii) said precipitated solid is rinsed with methanol; and (iv) said compound is dried, in vacuo, from about 40° C. to about 60° C.

According to another embodiment for the process for producing a compound of formula I, the compound of formula I is purified by recrystallization by dissolving said compound of formula I in from 4-8 volumes of 1-methyl-2-pyrrolidinone heated at 40-60° C., adding 4-8 volumes of methanol over 20-40 minutes while maintaining the temperature at 40-60° C., seeding the mixture with about 1% of the compound of formula I, diluting the seeded mixture with 4-8 volumes more of methanol at 40-60° C., then cooling slowly over 3-8 hours to about 0° C. The suspension is then filtered, rinsed 2-4 times with 5-15 volumes of methanol, then dried at 40-60° C. in vacuo.

(i) said compound of formula I is heated in a mixture of 1-methyl-2-pyrrolidinone and methanol from about 40° C. to about 60° C.; said mixture is cooled to about 0° C., then to about room temperature;

(ii) filtering precipitated solid from said mixture;

(iii) said precipitated solid is rinsed with methanol; and (iv) said compound is dried, in vacuo, from about 40° C. to about 60° C.

According to another embodiment for the process for producing a compound of formula I:
y is zero;
$R^1$ and $R^2$ are taken together to form a 3-tetrahydrofuranyl ring;
$R^9$ is hydrogen;
$R^{10}$ is a monocyclic ring system wherein said ring system comprises 5 ring atoms wherein no more than 2 ring atoms are selected from N, O or S and wherein up to 2 hydrogen atoms in said ring system are optionally replaced by $V^1$; and
$R^{11}$ is $(CH_2)_n$—Y, wherein n is zero, Y is $OR^8$, and $R^8$ is —$(C_1-C_4)$-straight or branched alkyl.

According to another embodiment for the process for producing a compound of formula I:
$R^{10}$ is 5-oxazolyl;
$R^{11}$ is methoxy, ethoxy or isopropoxy; and
$R^{16}$ is a phenyl ring optionally comprising up to 5 substituents independently selected from $(C_1-C_4)$-straight or branched alkyl, or $(CH_2)_n$—Z.

According to another embodiment for the process for producing a compound of formula I:
$R^{10}$ is 5-oxazolyl;
$R^{11}$ is methoxy; and
$R^{16}$ is a phenyl ring.

According to another embodiment for the process for producing a compound of formula I:
y is zero;
$R^1$ or $R^2$ is selected from hydrogen, methyl, ethyl or phenyl; and the other of $R^1$ or $R^2$ is selected from —$CH_2OH$, —$CH_2CN$, —$CH_2CH_2CN$, or —$CH_2N(CH_2CH_3)_2$; or wherein $R^1$ and $R^2$ are taken together to form a 3-tetrahydrofuranyl moiety;
$R^9$ is hydrogen, (S)-methyl, (S)-ethyl, or (S)-hydroxymethyl;
$R^{10}$ is selected from —C≡N or 5-oxazolyl; and
$R^{11}$ is methoxy, ethoxy or isopropoxy.

According to another embodiment for the process for producing a compound of formula I:
$R^1$ or $R^2$ is ethyl; and the other of $R^1$ or $R^2$ is —$CH_2CN$;
$R^9$ is (S)-methyl;
$R^{10}$ is selected from —C≡N or 5-oxazolyl; and
$R^{11}$ is methoxy.

According to another embodiment for the process for producing a compound of formula I:
$R^{16}$ is a monocyclic ring system consisting of 6 members per ring, wherein said ring system optionally comprises up to 2 heteroatoms selected from N, O, or S, and each $R^{16}$ optionally comprises up to 5 substituents independently selected from $(C_1-C_4)$-straight or branched alkyl, or $(CH_2)_n$—Z.

According to another embodiment for the process for producing a compound of formula I:
$R^{16}$ is a phenyl ring optionally comprising up to 5 substituents independently selected from $(C_1-C_4)$-straight or branched alkyl, or $(CH_2)_n$—Z.

According to another embodiment for the process for producing a compound of formula I:
$R^{16}$ is a phenyl ring.

Step 3 and Step 4 Embodiments

According to another embodiment, the present invention provides a process for preparing a compound of formula II:

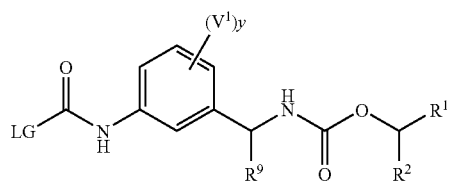

comprising the steps of:

(a) converting a compound of formula V:

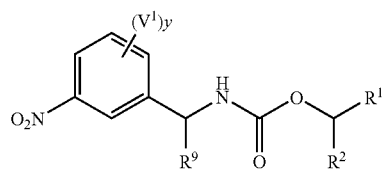

under suitable catalytic hydrogenation conditions to give a compound of formula IV:

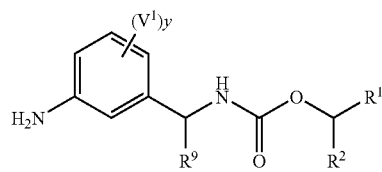

or a salt thereof; and (b) reacting said compound of formula IV with a compound of formula LGC(O)X, under suitable conditions, wherein:
X is a halogen;
LG is —$OR^{16}$; wherein $R^{16}$ is —$(C_1-C_6)$-straight or branched alkyl; —$(C_2-C_6)$-straight or branched alkenyl or alkynyl; or a monocyclic ring system consisting of 5 to 6 members per ring, wherein said ring system optionally comprises up to 3 heteroatoms selected from N, O, or S, and each $R^{16}$ optionally comprises up to 5 substituents independently selected from $(C_1-C_4)$-straight or branched alkyl, $(C_2-C_4)$ straight or branched alkenyl, or $(CH_2)_n$—Z;
wherein Z is selected from halogen, CN, $NO_2$, $CF_3$, $OCF_3$, OH, $S(C_1-C_4)$-alkyl, $SO(C_1-C_4)$-alkyl, $SO_2(C_1-C_4)$-alkyl, $NH_2$, $NH(C_1-C_4)$-alkyl, $N((C_1-C_4)$-alkyl$)_2$, COOH, $C(O)O(C_1-C_4)$-alkyl or $O(C_1-C_4)$-alkyl;
n is 0, 1, 2, 3, or 4; and
each of $R^1$ and $R^2$ is independently selected from hydrogen; —$CF_3$; —$(C_1-C_6)$-straight or branched alkyl; —$(C_2-C_6)$-straight or branched alkenyl or alkynyl; —$(C_1-C_6)$-straight or branched alkyl-$R^7$; —[($C_2$-$C_6$)-straight or branched alkenyl or alkynyl]-$R^7$ or —$R^7$; and wherein at least one of $R^1$ or $R^2$ is —($C_1$-$C_6$)-straight or branched alkyl-$R^7$; —[($C_2$-$C_6$)-straight or branched alkenyl or alkynyl]-$R^7$ or —$R^7$;

wherein up to 4 hydrogen atoms in any of said alkyl, alkenyl or alkynyl are optionally and independently replaced by $R^3$; or $R^1$ and $R^2$ are alternatively taken together to form a tetrahydrofuran ring, wherein up to 2 hydrogen atoms in said tetrahydrofuran ring are optionally replaced by —$OR^6$ or —$R^7$;

each $R_3$ is independently selected from halogen, CN, —$OR^4$, or —$N(R^5)_2$;

$R^4$ is selected from hydrogen, —($C_1$-$C_6$)-straight or branched alkyl, —($C_2$-$C_6$)-straight or branched alkenyl or alkynyl, —[($C_1$-$C_6$)-straight or branched alkyl]-$R^7$, —[($C_2$-$C_6$)-straight or branched alkenyl or alkynyl]-$R^7$, —C(O)—[($C_1$-$C_6$)-straight or branched alkyl], —C(O)—[($C_2$-$C_6$)-straight or branched alkenyl or alkynyl], —C(O)—[($C_1$-$C_6$)-straight or branched alkyl-$N(R^3)_2$, —C(O)—[($C_2$-$C_6$)-straight or branched alkenyl or alkynyl]-$N(R^8)_2$, —P(O)($OR^8$)$_2$, —P(O)($OR^8$)($R^8$), —C(O)—$R^7$, —$S(O)_2N(R^5)_2$, —[($C_1$-$C_6$)-straight or branched alkyl]-CN, or —[($C_2$-$C_6$)-straight or branched alkenyl or alkynyl]-CN;

wherein up to 4 hydrogen atoms in any of said alkyl, alkenyl or alkynyl are optionally and independently replaced by —C=O or Y;

Y is selected from halogen, CN, $NO_2$, $CF_3$, $OCF_3$, $SR^8$, $S(O)R^8$, $SO_2R^8$, $NHR^8$, $N(R^8)_2$, $COOR^8$ or $OR^8$;

each $R^5$ is independently selected from hydrogen, —($C_1$-$C_6$)-straight or branched alkyl, —($C_2$-$C_6$)-straight or branched alkenyl or alkynyl, —[($C_1$-$C_6$)-straight or branched alkyl]-$R^7$, —[($C_2$-$C_6$)-straight or branched alkenyl or alkynyl]-$R^7$, —[($C_1$-$C_6$)-straight alkyl]-CN, —[($C_2$-$C_6$)-straight or branched alkenyl or alkynyl]-CN, —[($C_1$-$C_6$)-straight or branched alkyl]-$OR^4$, —[($C_2$-$C_6$)-straight or branched alkenyl or alkynyl]-$R^4$, —C(O)—($C_1$-$C_6$)-straight or branched alkyl, —C(O)—[($C_2$-$C_6$)-straight or branched alkenyl or alkynyl], —C(O)—$R^7$, —C(O)O—$R^7$, —C(O)O—($C_1$-$C_6$)-straight or branched alkyl, —C(O)O—[($C_2$-$C_6$)-straight or branched alkenyl or alkynyl], —$S(O)_2$—($C_1$-$C_6$)-straight or branched alkyl, or —$S(O)_2$—$R^7$; or two $R^5$ moieties, when bound to the same nitrogen atom, are taken together with said nitrogen atom to form a 3 to 7-membered heterocyclic ring, wherein said heterocyclic ring optionally contains 1 to 3 additional heteroatoms independently selected from N, O, S, S(O) or $S(O)_2$;

wherein up to 4 hydrogen atoms in any of said alkyl, alkenyl or alkynyl are optionally and independently replaced by —C=O or Y;

$R^6$ is selected from —C(O)—$CH_3$, —$CH_2$—C(O)—OH, —$CH_2$—C(O)—O-tBu, —$CH_2$—CN, or —$CH_2$—C≡CH;

each $R_7$ is a monocyclic or bicyclic ring system wherein in said ring system:
i. each ring comprises 3 to 7 ring atoms independently selected from C, N, O or S;
ii. no more than 4 ring atoms are selected from N, O or S;
iii. any $CH_2$ is optionally replaced with C(O);
iv. any S is optionally replaced with S(O) or $S(O)_2$;
v. up to 3 hydrogen atoms in said monocyclic ring system or up to 6 hydrogens in said bicyclic ring system are optionally replaced by $V^1$;

each $R^8$ is independently selected from hydrogen, —($C_1$-$C_4$)-straight or branched alkyl, or —($C_2$-$C_4$)-straight or branched alkenyl;

wherein up to 4 hydrogen atoms in any of said alkyl or alkenyl are optionally and independently replaced by halogen, CN, $NO_2$, $CF_3$, $OCF_3$, $SR^{17}$, $S(O)R^{17}$, $SO_2R^{17}$, $NHR^{17}$, $N(R^{17})_2$, $COOR^{17}$ or $OR^{17}$;

wherein $R^{17}$ is selected from hydrogen, —($C_1$-$C_6$)-straight or branched alkyl, —($C_2$-$C_6$)-straight or branched alkenyl or alkynyl;

$R^9$ is selected from hydrogen, or —($C_1$-$C_6$)-straight or branched alkyl or ($C_3$-$C_6$)-cycloaliphatic;

wherein up to 4 hydrogen atoms in any of said alkyl, or cycloaliphatic are optionally and independently replaced by —C=O or Y;

provided that $R^{16}$ is not a halo-substituted ($C_2$-$C_3$)-straight alkyl.

According to another embodiment, the present invention provides a process for preparing a compound of formula II:

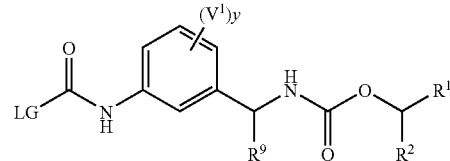

comprising the steps of:

(a) converting a compound of formula V to a compound of formula IV:

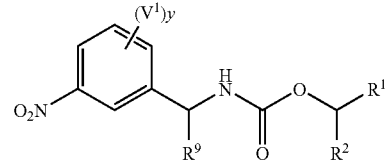

under suitable catalytic hydrogenation conditions to give a compound of formula IV:

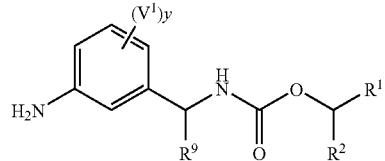

or a salt thereof;

and (b) reacting said compound of formula IV with a compound of formula LGC(O)X, under suitable conditions, wherein:
X is a halogen;
LG is —$OR^{16}$; wherein $R^{16}$ is —($C_1$-$C_6$)-straight or branched alkyl; —($C_2$-$C_6$)-straight or branched alkenyl or alkynyl; or a monocyclic ring system consisting of 5 to 6 members per ring, wherein said ring system optionally comprises up to 3 heteroatoms selected from N, O, or S, and each $R^{16}$ optionally comprises up to 5 substituents independently selected from $(C_1$-$C_4)$-straight or branched alkyl, $(C_2$-$C_4)$ straight or branched alkenyl, or $(CH_2)_n$—Z;
  wherein Z is selected from halogen, CN, $NO_2$, $CF_3$, $OCF_3$, OH, $S(C_1$-$C_4)$-alkyl, $SO(C_1$-$C_4)$-alkyl, $SO_2(C_1$-$C_4)$-alkyl, $NH_2$, $NH(C_1$-$C_4)$-alkyl, $N((C_1$-$C_4)$-alkyl$)_2$, COOH, $C(O)O(C_1$-$C_4)$-alkyl or $O(C_1$-$C_4)$-alkyl;
n is 0, 1, 2, 3, or 4; and
each of $R^1$ and $R^2$ is independently selected from hydrogen; —$CF_3$; —$(C_1$-$C_6)$-straight or branched alkyl; —$(C_2$-$C_6)$-straight or branched alkenyl or alkynyl; —$(C_1$-$C_6)$-straight or branched alkyl-$R^7$; —[$(C_2$-$C_6)$-straight or branched alkenyl or alkynyl]-$R^7$ or —$R^7$; and wherein at least one of $R^1$ or $R^2$ is —$(C_1$-$C_6)$-straight or branched alkyl-$R^7$; —[$(C_2$-$C_6)$-straight or branched alkenyl or alkynyl]-$R^7$ or —$R^7$;
  wherein up to 4 hydrogen atoms in any of said alkyl, alkenyl or alkynyl are optionally and independently replaced by $R^3$; or
$R^1$ and $R^2$ are alternatively taken together to form a tetrahydrofuran ring, wherein up to 2 hydrogen atoms in said tetrahydrofuran ring are optionally replaced by —$OR^6$ or —$R^7$;
each $R_3$ is independently selected from halogen, CN, —$OR^4$, or —$N(R^5)_2$;
$R^4$ is selected from hydrogen, —$(C_1$-$C_6)$-straight or branched alkyl, —$(C_2$-$C_6)$-straight or branched alkenyl or alkynyl, —[$(C_1$-$C_6)$-straight or branched alkyl]-$R^7$, —[$(C_2$-$C_6)$-straight or branched alkenyl or alkynyl]-$R^7$, —C(O)—[$(C_1$-$C_6)$-straight or branched alkyl], —C(O)—[$(C_2$-$C_6)$-straight or branched alkenyl or alkynyl], —C(O)—[$(C_1$-$C_6)$-straight or branched alkyl]-$N(R^3)_2$, —C(O)—[$(C_2$-$C_6)$-straight or branched alkenyl or alkynyl]-$N(R^8)_2$, —$P(O)(OR^8)_2$, —$P(O)(OR^8)(R^8)$, —C(O)—$R^7$, —$S(O)_2N(R^5)_2$, —[$(C_1$-$C_6)$-straight or branched alkyl]-CN, or —[$(C_2$-$C_6)$-straight or branched alkenyl or alkynyl]-CN;
  wherein up to 4 hydrogen atoms in any of said alkyl, alkenyl or alkynyl are optionally and independently replaced by —C=O or Y;
Y is selected from halogen, CN, $NO_2$, $CF_3$, $OCF_3$, $SR^8$, $S(O)R^8$, $SO_2R^8$, $NHR^8$, $N(R^8)_2$, $COOR^8$ or $OR^8$;
each $R^5$ is independently selected from hydrogen, —$(C_1$-$C_6)$-straight or branched alkyl, —$(C_2$-$C_6)$-straight or branched alkenyl or alkynyl, —[$(C_1$-$C_6)$-straight or branched alkyl]-$R^7$-[$(C_2$-$C_6)$-straight or branched alkenyl or alkynyl]-$R^7$, —[$(C_1$-$C_6)$-straight alkyl]-CN, —[$(C_2$-$C_6)$-straight or branched alkyl or alkynyl]-CN, —[$(C_1$-$C_6)$-straight or branched alkyl]-$OR^4$-[$(C_2$-$C_6)$-straight or branched alkenyl or alkynyl]-$OR^4$, —C(O)—$(C_1$-$C_6)$-straight or branched alkyl, —C(O)—[$(C_2$-$C_6)$-straight or branched alkenyl or alkynyl], —C(O)—$R^7$, —C(O)O—$R^7$, —C(O)O—$(C_1$-$C_6)$-straight or branched alkyl, —C(O)O—[$(C_2$-$C_6)$-straight or branched alkenyl or alkynyl], —$S(O)_2$—$(C_1$-$C_6)$-straight or branched alkyl, or —$S(O)_2$—$R^7$; or two $R^5$ moieties, when bound to the same nitrogen atom, are taken together with said nitrogen atom to form a 3 to 7-membered heterocyclic ring, wherein said heterocyclic ring optionally contains 1 to 3 additional heteroatoms independently selected from N, O, S, S(O) or $S(O)_2$;
  wherein up to 4 hydrogen atoms in any of said alkyl, alkenyl or alkynyl are optionally and independently replaced by —C=O or Y;
$R^6$ is selected from —C(O)—$CH_3$, —$CH_2$—C(O)—OH, —$CH_2$—C(O)—O-tBu, —$CH_2$—CN, or —$CH_2$—C≡CH;
each $R^7$ is a monocyclic or bicyclic ring system wherein in said ring system:
  i. each ring comprises 3 to 7 ring atoms independently selected from C, N, O or S;
  ii. no more than 4 ring atoms are selected from N, O or S;
  iii. any $CH_2$ is optionally replaced with C(O);
  iv. any S is optionally replaced with S(O) or $S(O)_2$;
  v. up to 3 hydrogen atoms in said monocyclic ring system or up to 6 hydrogens in said bicyclic ring system are optionally replaced by $V^1$;
each $R^8$ is independently selected from hydrogen, —$(C_1$-$C_4)$-straight or branched alkyl, or —$(C_2$-$C_4)$-straight or branched alkenyl;
  wherein up to 4 hydrogen atoms in any of said alkyl or alkenyl are optionally and independently replaced by halogen, CN, $NO_2$, $CF_3$, $OCF_3$, $SR^{17}$, $S(O)R^{17}$, $SO_2R^{17}$, $NHR^{17}$, $N(R^{17})_2$, $COOR^{17}$ or $OR^{17}$;
    wherein $R^{17}$ is selected from hydrogen, —$(C_1$-$C_6)$-straight or branched alkyl, —$(C_2$-$C_6)$-straight or branched alkenyl or alkynyl;
$R^9$ is selected from hydrogen, or —$(C_1$-$C_6)$-straight or branched alkyl or $(C_3$-$C_6)$-cycloaliphatic; and
  wherein up to 4 hydrogen atoms in any of said alkyl, or cycloaliphatic are optionally and independently replaced by —C=O or Y.

According to another embodiment for the process for producing a compound of formula II:
in step (a) said suitable hydrogenation conditions comprise one or more of the following: a suitable metal catalyst; a suitable solvent selected from a protic solvent, a polar aprotic solvent, a non-polar aprotic solvent or any mixtures thereof; a suitable reaction atmosphere of hydrogen gas at a suitable pressure; and a suitable reaction temperature; and
in step (b) said suitable conditions for reacting said intermediate of formula IV with a compound of formula LGC(O)X comprises one or more of the following: a suitable solvent selected from a protic solvent, an aprotic solvent or mixtures thereof; a suitable inorganic or organic base; a suitable reaction atmosphere; and a suitable reaction temperature.

According to another embodiment for the process for producing a compound of formula II, said process comprises one or more of the following:
in step (a) said metal catalyst is between about 1% to about 30% by weight palladium metal on carbon; said protic solvent is selected from a $(C_1$-$C_5)$-straight or branched alkyl alcohol; said aprotic solvent is selected from an ester-type solvent; said reaction atmosphere comprises hydrogen gas at between about one to about ten atmospheres of pressure; and said reaction temperature is between about 20° C. to about 60° C.; and
in step (b) said suitable solvent is a mixture of water and an aprotic solvent selected from ethyl acetate, isopropyl acetate, n-butyl acetate, benzene, toluene, xylene, dichloromethane, dichloroethane, chloroform, trifluorotoluene, ethyl ether, isopropyl ether, or methyl t-butyl ether; said reaction atmosphere is selected from air, nitrogen or argon; said inorganic base is selected from $Na_2SO_4$, $Na_2CO_3$, $K_2CO_3$, $Cs_2CO_3$, $Li_2CO_3$, $NaHCO_3$, or $KHCO_3$; and said reaction temperature is between about 20° C. and about 80° C.

According to another embodiment for the process for producing a compound of formula II, said process comprises one or more of the following:
(a) said metal catalyst is between about 5% to about 10% by weight palladium metal on carbon; said protic solvent is selected from methanol, ethanol, or isopropanol; said aprotic solvent is selected from ethyl acetate or isopropyl acetate; said reaction atmosphere of hydrogen gas is between about one to about eight atmospheres of pressure; and said reaction temperature is between about 20° C. to about 40° C.; and (b) said suitable solvent is a mixture of water and an aprotic solvent selected from ethyl acetate or isopropyl acetate; said reaction atmosphere is selected from nitrogen or argon; said inorganic base is selected from $Na_2SO_4$; and said reaction temperature is between about 40° C. and about 60° C.

According to another embodiment for the process for producing a compound of formula II:

(a) said metal catalyst is about 5% by weight palladium metal on carbon; said aprotic solvent is ethyl acetate; said reaction atmosphere of hydrogen gas is between about four and eight atmospheres of pressure; and said reaction temperature is between about 20° C. to about 30° C.; and (b) said suitable solvent is a mixture of water and an aprotic solvent selected from ethyl acetate or isopropyl acetate; said reaction atmosphere is selected from nitrogen; and said reaction temperature is between about 40° C. and about 60° C.

According to another embodiment for the process for producing a compound of formula II:

(a) said metal catalyst is about 5% by weight palladium metal on carbon (50% wet); said aprotic solvent is ethyl acetate; said reaction atmosphere of hydrogen gas is about six to seven atmospheres of pressure; and said temperature is about 25° C.; and (b) said suitable solvent is a mixture of water and an aprotic solvent selected from ethyl acetate or isopropyl acetate; said reaction atmosphere is selected from nitrogen; said inorganic base is selected from $Na_2SO_4$; and said reaction temperature is about 50° C.

According to another embodiment for the process for producing a compound of formula II:

(a) said metal catalyst is about 5% by weight palladium metal on carbon (50% wet); said aprotic solvent is isopropyl acetate; said reaction atmosphere of hydrogen gas is about 12-18 psi; and said temperature is about 60° C.; and (b) said suitable solvent is a mixture of water and an aprotic solvent selected from isopropyl acetate; said reaction atmosphere is selected from nitrogen; said inorganic base is selected from $Na_2SO_4$; and said reaction temperature is about 70° C.

According to another embodiment for the process for producing a compound of formula II:

$R^{16}$ is a monocyclic ring system consisting of 6 members per ring, wherein said ring system optionally comprises up to 2 heteroatoms selected from N, O, or S, and each $R^{16}$ optionally comprises up to 5 substituents independently selected from $(C_1-C_4)$-straight or branched alkyl, or $(CH_2)_n$—Z.

According to another embodiment for the process for producing a compound of formula II:

$R^{16}$ is a phenyl ring optionally comprising up to 5 substituents independently selected from $(C_1-C_4)$-straight or branched alkyl, or $(CH_2)_n$—Z.

According to another embodiment for the process for producing a compound of formula II:

$R^{16}$ is a phenyl ring.

According to another embodiment for the process for producing a compound of formula II:

y is zero;

$R^1$ and $R^2$ are taken together to form a 3-tetrahydrofuranyl ring; and $R^9$ is hydrogen.

According to another embodiment for the process for producing a compound of formula II:

y is zero;

$R^1$ or $R^2$ is selected from hydrogen, methyl, ethyl or phenyl; and the other of $R^1$ or $R^2$ is selected from —$CH_2OH$, —$CH_2CN$, —$CH_2CH_2CN$, or —$CH_2N(CH_2CH_3)_2$; or wherein $R^1$ and $R^2$ are taken together to form a 3-tetrahydrofuranyl moiety; and $R^9$ is hydrogen, (S)-methyl, (S)-ethyl, or (S)-hydroxymethyl.

According to another embodiment for the process for producing a compound of formula II:

$R^1$ or $R^2$ is ethyl; and the other of $R^1$ or $R^2$ is —$CH_2CN$; and $R^9$ is (S)-methyl.

Step 1 and Step 2 Embodiments

According to another embodiment for the process for producing a compound of formula II, said compound of formula V:

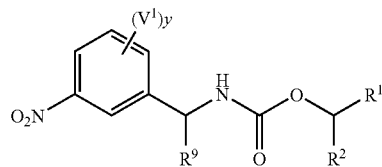

is prepared by a process comprising the steps of:

(a) reacting a compound of formula VII with a phosgene reagent or a suitable phosgene reagent equivalent, under suitable conditions, to prepare a compound of formula VIII;

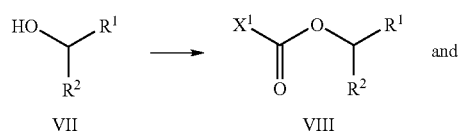

(b) reacting said compound of formula VIII, or a synthetically acceptable analog or derivative thereof, with a compound of formula IX, or a synthetically acceptable analog or derivative thereof, under suitable conditions:

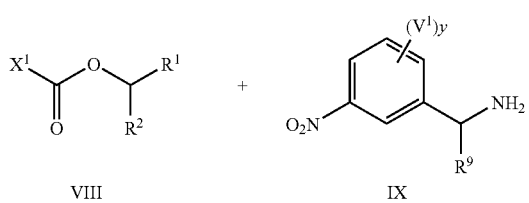

wherein:

$X^1$ is halogen;

y is zero;

$R^1$ or $R^2$ is selected from hydrogen, methyl, ethyl or phenyl; and the other of $R^1$ or $R^2$ is selected from —$CH_2OH$, —$CH_2CN$, —$CH_2CH_2CN$, or —$CH_2N(CH_2CH_3)_2$; or wherein $R^1$ and $R^2$ are taken together to form a 3-tetrahydrofuranyl moiety;

$R^9$ is hydrogen, (S)-methyl, (S)-ethyl, or (S)-hydroxymethyl;

each $V^1$ is independently selected from halogen, $NO_2$, CN, $OR^{12}$, $OC(O)R^{13}$, $OC(O)R^{12}OC(O)OR^{13}$, $OC(O)OR^{12}$, $OC(O)N(R^{13})_2$, $OP(O)(OR^{13})_2$, $SR^{13}$, $SR^{12}$, $S(O)_3R^{13}$, $S(O)R^{12}R^{13}$, $SO_2R^{12}$, $SO_2N(R^{13})_2$, $SO_2NR^{12}R^{13}$, $SO_3R^{12}$, $C(O)R^{13}$, $C(O)OR^{13}$, $C(O)R^{12}$, $C(O)OR^{12}$, $NC(O)C(O)R^{13}$, $NC(O)C(O)R^{12}$, $NC(O)C(O)OR^{13}$, $NC(O)C(O)N(R^{13})_2$, $C(O)N(R^{13})_2$, $C(O)N(OR^{13})R^{13}$, $C(O)N(OR^{13})R^{12}$, $C(NOR^{13})R^{13}$, $C(NOR^{13})R^{12}$, $N(R^{13})_2$, $NR^{13}C(O)R^{12}$, $NR^{13}C(O)R^{13}R^{13}$, $NR^{12}C(O)R^{12}$, $NR^{13}C(O)OR^{13}$, $NR^{13}C(O)OR^{12}$, $NR^{13}C(O)N(R^{13})_2$, $NR^{13}C(O)NR^{12}R^{13}$, $NR^{13}SO_2R^{13}$, $NR^{13}SO_2R^{12}$, $NR^{13}SO_2N(R^{13})_2$, $NR^{13}SO_2NR^{13}R^{12}$, $N(OR^{13})R^{13}$, $N(OR^{13})R^{12}$, $P(O)(OR^{13}))N(R^{13})_2$, and $P(O)(OR^{13})_2$;

wherein each $R^{12}$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S may be substituted with C(O); and each $R^{12}$ optionally comprises up to 3 substituents selected from $R^{11}$;

wherein each $R^{13}$ is independently selected from H, $(C_1-C_4)$-straight or branched alkyl, or $(C_2-C_4)$ straight or branched alkenyl; and wherein each $R^{13}$ optionally comprises a substituent that is $R^{14}$;

wherein $R^{14}$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S maybe substituted with C(O); and each $R^{14}$ optionally comprises up to 2 substituents independently chosen from H, $(C_1-C_4)$-straight or branched alkyl, or $(C_2-C_4)$ straight or branched alkenyl, 1,2-methylenedioxy, 1,2-ethylenedioxy, or $(CH_2)_n$—Z;

wherein Z is selected from halogen, CN, $NO_2$, $CF_3$, $OCF_3$, OH, $S(C_1-C_4)$-alkyl, $SO(C_1-C_4)$-alkyl, $SO_2(C_1-C_4)$-alkyl, $NH_2$, $NH(C_1-C_4)$-alkyl, $N((C_1-C_4)$-alkyl)$_2$, $N((C_1-C_4)$-alkyl)$R^{15}$, COOH, $C(O)O(C_1-C_4)$-alkyl or $O(C_1-C_4)$-alkyl;

wherein n is 0, 1, 2, 3, or 4; and wherein $R^{15}$ is an amino protecting group; and wherein any carbon atom in any $R^{13}$ is optionally replaced by O, S, SO, $SO_2$, NH, or $N(C_1-C_4)$-alkyl.

According to another embodiment for the process for producing a compound of formula V, said process comprises one or more of the following:

in step (a) said phosgene reagent is about a 10% to about a 30% solution of phosgene in toluene; said suitable conditions comprise a suitable solvent selected from a nonpolar aprotic solvent; a suitable organic base; a suitable reaction atmosphere; a suitable reaction temperature; and a suitable reaction time; and in step (b) said suitable conditions comprise a suitable solvent selected from a protic solvent, an aprotic solvent, or mixtures thereof; a suitable inorganic or organic base; a suitable reaction atmosphere; a suitable reaction temperature; and a suitable reaction time.

According to another embodiment for the process for producing a compound of formula V, said process comprises one or more of the following:

in step (a) said phosgene reagent is about a 20% solution of phosgene in toluene; said nonpolar aprotic solvent is benzene or toluene; said organic base is pyridine; said suitable reaction atmosphere is nitrogen or argon; said suitable reaction temperature is between about 20° C. and about 60° C.; and said suitable reaction time is between about 1 hour to about 48 hours;

in step (b) said suitable conditions comprise a suitable solvent mixture; a suitable organic base; a suitable reaction atmosphere; a suitable reaction temperature; and a suitable reaction time; and said suitable solvent mixture comprises a mixture of a protic solvent and an aprotic solvent wherein said protic solvent is water, and wherein said aprotic solvent is selected ethyl acetate, isopropyl acetate, n-butyl acetate, benzene, toluene, xylene, dichloromethane, dichloroethane, chloroform, trifluorotoluene, ethyl ether, isopropyl ether, or methyl t-butyl ether; said inorganic base is selected from $Na_2CO_3$, $K_2CO_3$, $Cs_2CO_3$, $Li_2CO_3$, $NaHCO_3$, $KHCO_3$, NaOH, KOH, LiOH; said reaction atmosphere is selected from air, nitrogen or argon; said reaction temperature is between about 20° C. and about 80° C.; and said reaction time is between about 30 minutes to about 24 hours.

According to another embodiment for the process for producing a compound of formula V, in step (b) said suitable solvent mixture comprises water and toluene; said inorganic base is selected from $Na_2CO_3$; said reaction atmosphere is selected from nitrogen; said reaction temperature is about 50° C.; and said reaction time is between about 2.0 hours.

According to another embodiment for the process for producing a compound of formula V:

$X^1$ is chlorine.

According to another embodiment for the process for producing a compound of formula V:

y is zero;

$R^1$ and $R^2$ are taken together to form a 3-tetrahydrofuranyl moiety; and $R^9$ is hydrogen, or (S)-methyl.

According to another embodiment for the process for producing a compound of formula V:

$R^1$ or $R^2$ is selected from hydrogen, methyl, ethyl or phenyl; and the other of $R^1$ or $R^2$ is selected from —$CH_2OH$, —$CH_2CN$, —$CH_2CH_2CN$, or —$CH_2N(CH_2CH_3)_2$; and $R^9$ is hydrogen or (S)-methyl.

According to another embodiment the present invention provides a compound of formula Va:

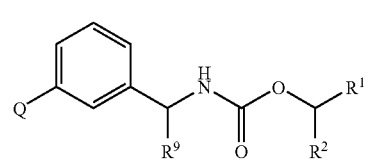

Va or a salt thereof, wherein:

Q is $NO_2$ or $NH_2$;

each of $R^1$ and $R^2$ is independently selected from hydrogen; —$CF_3$; —$(C_1-C_6)$-straight or branched alkyl; —$(C_2-C_6)$-straight or branched alkenyl or alkynyl; —$(C_1-C_6)$-straight or branched alkyl-$R^7$; —[$(C_2-C_6)$-straight or branched alkenyl or alkynyl]-$R^7$ or —$R^7$; and wherein at least one of $R^1$ or $R^2$ is —$(C_1-C_6)$-straight or branched alkyl-$R^7$; —[$(C_2-C_6)$-straight or branched alkenyl or alkynyl]-$R^7$ or —$R^7$;

wherein up to 4 hydrogen atoms in any of said alkyl, alkenyl or alkynyl are optionally and independently replaced by $R^3$; or R$^1$ and R$^2$ are alternatively taken together to form a tetrahydrofuran ring, wherein up to 2 hydrogen atoms in said tetrahydrofuran ring are optionally replaced by —OR$^6$ or —R$^7$;

each R$_3$ is independently selected from halogen, CN, —OR$^4$, or —N(R$^5$)$_2$;

R$^4$ is selected from hydrogen, —(C$_1$-C$_6$)-straight or branched alkyl, —(C$_2$-C$_6$)-straight or branched alkenyl or alkynyl, —[(C$_1$-C$_6$)-straight or branched alkyl]-R$^7$, —[(C$_2$-C$_6$)-straight or branched alkenyl or alkynyl]-R$^7$, —C(O)—[(C$_1$-C$_6$)-straight or branched alkyl], —C(O)—[(C$_2$-C$_6$)-straight or branched alkenyl or alkynyl], —C(O)—[(C$_1$-C$_6$)-straight or branched alkyl]-N(R$^8$)$_2$, —C(O)—[(C$_2$-C$_6$)-straight or branched alkenyl or alkynyl]-N(R$^8$)$_2$, —P(O)(OR$^8$)$_2$, —P(O)(OR$^8$)(R$^8$), —C(O)—R$^7$, —S(O)$_2$N(R$^5$)$_2$-[(C$_1$-C$_6$)-straight or branched alkyl]-CN, or —[(C$_2$-C$_6$)-straight or branched alkenyl or alkynyl]-CN;
wherein up to 4 hydrogen atoms in any of said alkyl, alkenyl or alkynyl are optionally and independently replaced by —C=O or Y;

Y is selected from halogen, CN, NO$_2$, CF$_3$, OCF$_3$, SR$^8$, S(O)R$^8$, SO$_2$R$^8$, NHR$^8$, N(R$^8$)$_2$, COOR$^8$ or OR$^8$;

each R$^5$ is independently selected from hydrogen, —(C$_1$-C$_6$)-straight or branched alkyl, —(C$_2$-C$_6$)-straight or branched alkenyl or alkynyl, —[(C$_1$-C$_6$)-straight or branched alkyl]-R$^7$, —[(C$_2$-C$_6$)-straight or branched alkenyl or alkynyl]-R$^7$, —[(C$_1$-C$_6$)-straight alkyl]-CN, —[(C$_2$-C$_6$)-straight or branched alkenyl or alkynyl]-CN, —[(C$_1$-C$_6$)-straight or branched alkyl]-OR$^4$, —[(C$_2$-C$_6$)-straight or branched alkenyl or alkynyl]-OR$^4$, —C(O)—(C$_1$-C$_6$)-straight or branched alkyl, —C(O)—[(C$_2$-C$_6$)-straight or branched alkenyl or alkynyl], —C(O)—R$^7$, —C(O)O—R$^7$, —C(O)O—(C$_1$-C$_6$)-straight or branched alkyl, —C(O)O—[(C$_2$-C$_6$)-straight or branched alkenyl or alkynyl], —S(O)$_2$—(C$_1$-C$_6$)-straight or branched alkyl, or —S(O)$_2$—R$^7$; or two R$^5$ moieties, when bound to the same nitrogen atom, are taken together with said nitrogen atom to form a 3 to 7-membered heterocyclic ring, wherein said heterocyclic ring optionally contains 1 to 3 additional heteroatoms independently selected from N, O, S, S(O) or S(O)$_2$;
wherein up to 4 hydrogen atoms in any of said alkyl, alkenyl or alkynyl are optionally and independently replaced by —C=O or Y;

R$^6$ is selected from —C(O)—CH$_3$, —CH$_2$—C(O)—OH, —CH$_2$—C(O)—O-tBu, —CH$_2$—CN, or —CH$_2$—C≡CH;

each R$^7$ is a monocyclic or bicyclic ring system wherein in said ring system:
  i. the ring comprises 5 to 7 ring atoms independently selected from C, N, O or S;
  ii. no more than 4 ring atoms are selected from N, O or S;
  iii. any CH$_2$ is optionally replaced with C(O);
  iv. any S is optionally replaced with S(O) or S(O)$_2$; and
  v. up to 3 hydrogen atoms in said monocyclic ring system are optionally replaced by V$^1$;

each R$^8$ is independently selected from hydrogen, —(C$_1$-C$_4$)-straight or branched alkyl, or —(C$_2$-C$_4$)-straight or branched alkenyl;
wherein up to 4 hydrogen atoms in any of said alkyl or alkenyl are optionally and independently replaced by halogen, CN, NO$_2$, CF$_3$, OCF$_3$, SR$^{17}$, S(O)R$^{17}$, SO$_2$R$^{17}$, NHR$^{17}$, N(R$^{17}$)$_2$, COOR$^{17}$ or OR$^{17}$;
wherein R$^{17}$ is selected from hydrogen, —(C$_1$-C$_6$)-straight or branched alkyl, —(C$_2$-C$_6$)-straight or branched alkenyl or alkynyl;

R$^9$ is selected from hydrogen, or —(C$_1$-C$_6$)-straight or branched alkyl or (C$_3$-C$_6$)-cycloaliphatic;
wherein up to 4 hydrogen atoms in any of said alkyl, or cycloaliphatic are optionally and independently replaced by —C=O or Y;

provided that;
(a) when R$^1$ is hydrogen and R$^2$ is CH$_2$Ph, then R$^9$ is not CH$_2$OR$^8$, CH$_2$CO$_2$R$^8$, CO$_2$R$^8$, CN, or C(O)NH$_2$; and provided that the following compounds are excluded;
(b) methyl 2-(methoxycarbonyl)-1-(3-nitrophenyl) allylcarbamate;
(c) methyl 2-hydroxy-1-(3-nitrophenyl)propylcarbamate;
(d) allyl 2-(ethoxycarbonyl)-1-(3-nitrophenyl)ethylcarbamate;
(e) ethyl cyano(3-nitrophenyl)methylcarbamate; and
(f) ethyl 2-(ethoxycarbonyl)-1-(3-nitrophenyl)-3-oxobutylcarbamate.

According to another embodiment the present invention provides a compound of formula Va:

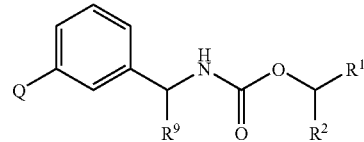

Va or a salt thereof, wherein:

Q is NO$_2$ or NH$_2$;

each of R$^1$ and R$^2$ is independently selected from hydrogen; —CF$_3$; —(C$_1$-C$_6$)-straight or branched alkyl; —(C$_2$-C$_6$)-straight or branched alkenyl or alkynyl; —(C$_1$-C$_6$)-straight or branched alkyl-R$^7$; —[(C$_2$-C$_6$)-straight or branched alkenyl or alkynyl]-R$^7$ or —R$^7$; and wherein at least one of R$^1$ or R$^2$ is —(C$_1$-C$_6$)-straight or branched alkyl-R$^7$; —[(C$_2$-C$_6$)-straight or branched alkenyl or alkynyl]-R$^7$ or —R$^7$;
wherein up to 4 hydrogen atoms in any of said alkyl, alkenyl or alkynyl are optionally and independently replaced by R$^3$; or R$^1$ and R$^2$ are alternatively taken together to form a tetrahydrofuran ring, wherein up to 2 hydrogen atoms in said tetrahydrofuran ring are optionally replaced by —OR$^6$ or —R$^7$;

each R$_3$ is independently selected from halogen, CN, —OR$^4$, or —N(R$^5$)$_2$;

R$^4$ is selected from hydrogen, —(C$_1$-C$_6$)-straight or branched alkyl, —(C$_2$-C$_6$)-straight or branched alkenyl or alkynyl, —[(C$_1$-C$_6$)-straight or branched alkyl]-R$^7$, —[(C$_2$-C$_6$)-straight or branched alkenyl or alkynyl]-R$^7$, —C(O)—[(C$_1$-C$_6$)-straight or branched alkyl], —C(O)—[(C$_2$-C$_6$)-straight or branched alkenyl or alkynyl], —C(O)—[(C$_1$-C$_6$)-straight or branched alkyl]-N(R$^8$)$_2$, —C(O)—[(C$_2$-C$_6$)-straight or branched alkenyl or alkynyl]-N(R$^8$)$_2$, —P(O)(OR$^8$)$_2$, —P(O)(OR$^8$)(R$^8$), —C(O)—R$^7$, —S(O)$_2$N(R$^5$)$_2$-[(C$_1$-C$_6$)-straight or branched alkyl]-CN, or —[(C$_2$-C$_6$)-straight or branched alkenyl or alkynyl]-CN;
wherein up to 4 hydrogen atoms in any of said alkyl, alkenyl or alkynyl are optionally and independently replaced by —C=O or Y;

Y is selected from halogen, CN, NO$_2$, CF$_3$, OCF$_3$, SR$^8$, S(O)R$^8$, SO$_2$R$^3$, NHR$^8$, N(R$^8$)$_2$, COOR$^8$ or OR$^8$;

each R$^5$ is independently selected from hydrogen, —(C$_1$-C$_6$)-straight or branched alkyl, —(C$_2$-C$_6$)-straight or branched alkenyl or alkynyl, —[(C$_1$-C$_6$)-straight or branched alkyl]-R$^7$, —[(C$_2$-C$_6$)-straight or branched alkenyl or alkynyl]-R$^7$, —[(C$_1$-C$_6$)-straight alkyl]-CN, —[(C$_2$-C$_6$)-straight or branched alkenyl or alkynyl]-CN, —[($C_1$-$C_6$)-straight or branched alkyl]-OR$^4$, —[($C_2$-$C_6$)-straight or branched alkenyl or alkynyl]-R$^4$, —C(O)—($C_1$-$C_6$)-straight or branched alkyl, —C(O)—[($C_2$-$C_6$)-straight or branched alkenyl or alkynyl], —C(O)—R$^7$, —C(O)O—R$^7$, —C(O)O—($C_1$-$C_6$)-straight or branched alkyl, —C(O)O—[($C_2$-$C_6$)-straight or branched alkenyl or alkynyl], —S(O)$_2$—($C_1$-$C_6$)-straight or branched alkyl, or —S(O)$_2$—R$^7$; or two R$^5$ moieties, when bound to the same nitrogen atom, are taken together with said nitrogen atom to form a 3 to 7-membered heterocyclic ring, wherein said heterocyclic ring optionally contains 1 to 3 additional heteroatoms independently selected from N, O, S, S(O) or S(O)$_2$;
  wherein up to 4 hydrogen atoms in any of said alkyl, alkenyl or alkynyl are optionally and independently replaced by —C=O or Y;
R$^6$ is selected from —C(O)—CH$_3$, —CH$_2$—C(O)—OH, —CH$_2$—C(O)—O-tBu, —CH$_2$—CN, or —CH$_2$—C≡CH;
each R$_7$ is a monocyclic or bicyclic ring system wherein in said ring system:
  i. the ring comprises 5 to 7 ring atoms independently selected from C, N, O or S;
  ii. no more than 4 ring atoms are selected from N, O or S;
  iii. any CH$_2$ is optionally replaced with C(O);
  iv. any S is optionally replaced with S(O) or S(O)$_2$; and
  v. up to 3 hydrogen atoms in said monocyclic ring system are optionally replaced by V$^1$;
each R$^8$ is independently selected from hydrogen, —($C_1$-$C_4$)-straight or branched alkyl, or —($C_2$-$C_4$)-straight or branched alkenyl;
  wherein up to 4 hydrogen atoms in any of said alkyl or alkenyl are optionally and independently replaced by halogen, CN, NO$_2$, CF$_3$, OCF$_3$, SR$^{17}$, S(O)R$^{17}$, SO$_2$R$^{17}$, NHR$^{17}$, N(R$^{17}$)$_2$, COOR$^{17}$ or OR$^{17}$;
    wherein R$^{17}$ is selected from hydrogen, —($C_1$-$C_6$)-straight or branched alkyl, —($C_2$-$C_6$)-straight or branched alkenyl or alkynyl;
R$^9$ is selected from hydrogen, or —($C_1$-$C_6$)-straight or branched alkyl or ($C_3$-$C_6$)-cycloaliphatic; and
  wherein up to 4 hydrogen atoms in any of said alkyl, or cycloaliphatic are optionally and independently replaced by —C=O or Y.
According to another embodiment for compounds of formula Va:
R$^1$ and R$^2$ are taken together to form a 3-tetrahydrofuranyl ring; and
R$^9$ is hydrogen.
According to yet another embodiment for compounds of formula Va:
R$^1$ or R$^2$ is selected from hydrogen, methyl, ethyl or phenyl; and the other of R$^1$ or R$^2$ is selected from —CH$_2$OH, —CH$_2$CN, —CH$_2$CH$_2$CN, or —CH$_2$N(CH$_2$CH$_3$)$_2$; or wherein R$^1$ and R$^2$ are taken together to form a 3-tetrahydrofuranyl moiety; and
R$^9$ is hydrogen, (S)-methyl, (S)-ethyl, or (S)-hydroxymethyl.
According to another embodiment for compounds of formula Va:
R$^1$ or R$^2$ is ethyl; and the other of R$^1$ or R$^2$ is —CH$_2$CN; and
R$^9$ is (S)-methyl.
Pharmaceutically acceptable salts of the compounds of this invention include those derived from pharmaceutically acceptable inorganic and organic acids and bases. Examples of suitable acid salts include acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

Compounds of formula III, formula IV and IX may be conveniently prepared as salts. Specific acid salts useful for producing salt of compounds of formula III, IV and IX may be selected from acids known in the art. See, e.g., "Practical Process, Research & Development," Anderson, Neal G., Academic Press, 2000, the contents of which are incorporated herein by reference.

In order that this invention be more fully understood, the following schemes and examples are set forth. The schemes and examples are offered by way of illustration, not limitation.

Scheme 2:

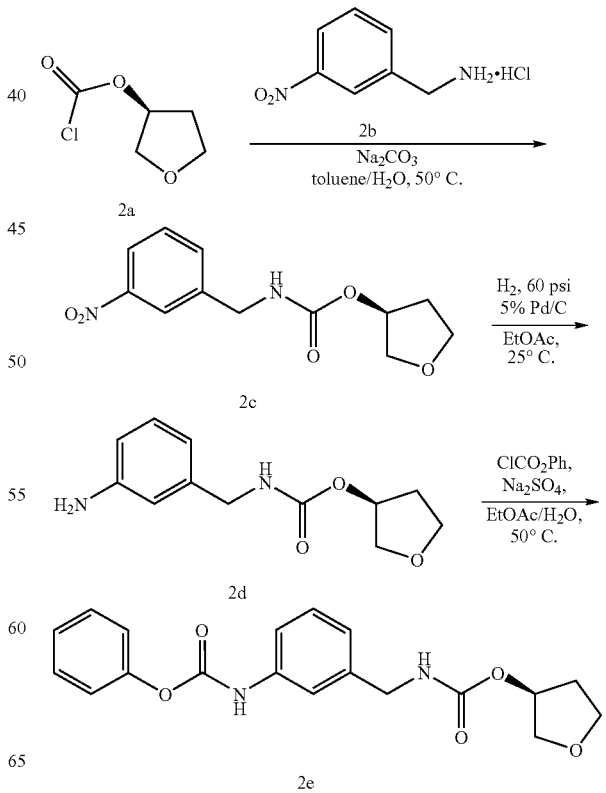

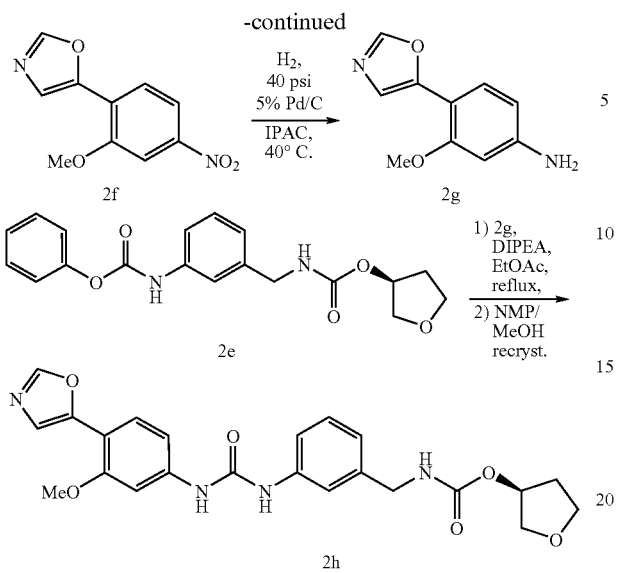

Scheme 2 above exemplifies a process embodiment of the present invention used to prepare compound 2h. Therein, commercially available chloroformate 2a is reacted under biphasic basic conditions at 50° C. with commercially available 3-nitrobenzylamine hydrochloride 2b to give carbamate 2c. Catalytic hydrogenation of nitro intermediate 2c using 5% Pd/C in EtOAc afforded aniline 2d in high yield which was reacted immediately with phenyl chloroformate in a warm biphasic mixture to give phenyl carbamate 2e as a crystalline solid. Catalytic hydrogenation of commercially available nitro intermediate 2f using 5% Pd/C in i-PrOAc afforded aniline 2g. Finally, aniline 2g and carbamate 2e were refluxed in the presence of Hunigs base to give crude urea 2h that was further purified by recrystallization from 1-methyl-2-pyrrolidinone and methanol.

Scheme 2A:

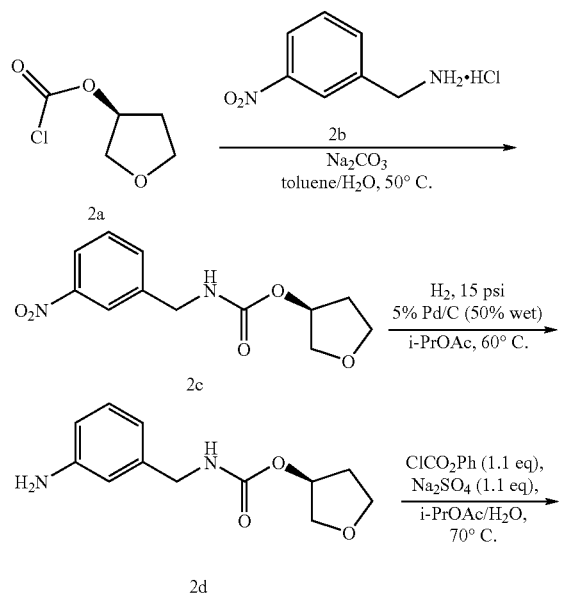

Scheme 2A above exemplifies another process embodiment of the present invention used to prepare compound 2h. Therein, commercially available chloroformate 2a is reacted under biphasic basic conditions at 50° C. with commercially available 3-nitrobenzylamine hydrochloride 2b to give carbamate 2c. Catalytic hydrogenation of nitro intermediate 2c using 5% Pd/C (50% wet) in EtOAc afforded aniline 2d in high yield which was reacted immediately with phenyl chloroformate (1.1 eq) and sodium sulfate (1.1 eq) in a warm biphasic mixture to give phenyl carbamate 2e as a solid. Catalytic hydrogenation of commercially available nitro intermediate 2f using 1% Pt, 2% Vanadium on carbon (64% wet, 2.0 wt % dry, Degussa Type CF1082) in i-PrOAc afforded aniline 2g. Finally, aniline 2g and carbamate 2e were refluxed in ethyl acetate in the presence of Hunigs base (1.0 eq) to give crude urea 2h that was further purified by recrystallization from 1-methyl-2-pyrrolidinone and methanol.

EXAMPLES

$^1$H-NMR spectra were taken in solution using an appropriate deuterio solvent and were recorded at 500 MHz using a Bruker AMX 500 instrument. Mass spec. samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spec. analysis consisted of acetonitrile-water mixtures with 0.2% formic acid as a modifier.

As used herein, the term "R$_t$(min)" refers to the HPLC retention time, in minutes, associated with the compound. The HPLC retention times listed were either obtained from the mass spec. data or using the following method:

Instrument: Agilent 1100 HPLC;
Column: Atlantis dC-18, 4.6×100 mm, 3 micron particle size;
Mobile Phase A: 0.025% (v/v)H$_3$PO$_4$ in H$_2$O;
Mobile Phase B: 100% CH$_3$CN;
Gradient/Gradient Time:
0 min., Mobile Phase B at 10%;
1 min., Mobile Phase B at 10%;
10 min., Mobile Phase B at 55%;
15 min., Mobile Phase B at 95%;
15.1 min., Mobile Phase B at 10%;
17 min., Mobile Phase B at 10%;
Flow Rate: 1.5 ml/min;
Detector Wavelength: 210 nM;
Column Temperature: 35° C.;
Injection Volume: 10 microliters Chemical naming for selected compounds herein was accomplished using the naming program provided by CambridgeSoft Corporations ChemDraw Ultra®, version 7.0.1 and version 8.0.

Solvents were purchased commercially (Baker, Aldrich) and kept substantially dry under nitrogen. Unless specified otherwise, all temperatures refer to internal reaction temperatures.

Experimental Procedures:

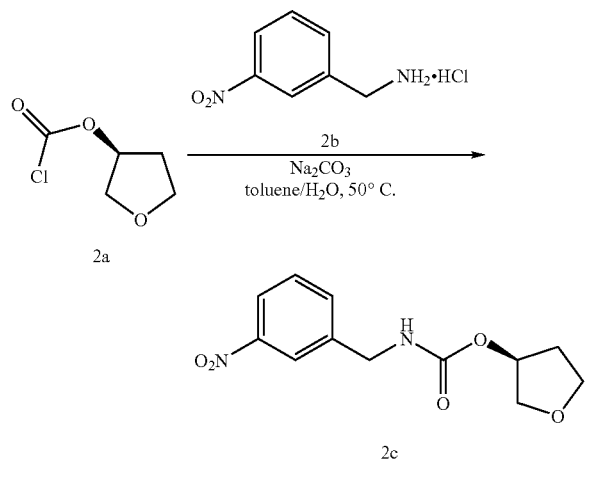

(S)-tetrahydrofuran-3-yl 3-nitrobenzylcarbamate (2c)

Added 13.84 g Na$_2$CO$_3$ to a 500 ml three neck round bottom flask equipped with a mechanical stirrer, addition funnel, and thermocouple. Then added 86 ml water and stirred until full dissolution at room temperature. 20 g 3-nitrobenzylamine HCl 2b was then added, followed by 154 ml toluene. The mixture was heated to 50° C. wherein a clear biphasic solution results. Added a 20% w/w solution of (S)-tetrahydrofuran-3-yl chloroformate, 2a (16 g) in toluene (80 ml) dropwise over 45 minutes wherein very little exotherm was noted. The reaction mixture was stirred for an additional 1 hour before the layers were separated at 50° C. The mixture was concentrated to ~85 ml, cooled to 0° C. and stirred for 1 hour at 0° C. Precipitated product was collected by filtration and dried for 18 hours at 53° C. to give 26.64 g (94.4% yield, 99.90% a/a) of (S)-tetrahydrofuran-3-yl 3-nitrobenzylcarbamate (2c) as a white crystalline solid with consistent $^1$H NMR (500 MHz, d$_6$-DMSO): 8.10 (m, 2H); 7.90 (m, 1H); 7.70 (d, 1H); 7.62 (t, 1H); 5.10 (br, 1H); 4.30 (d, 2H); 3.72 (m, 4H); 2.10 (m, 1H); 1.87 (m, 1H) ppm.

{3-[((S)-tetrahydro-furan-3-yloxycarbonylamino)-methyl]-phenyl}-carbamic acid phenyl ester (2e)

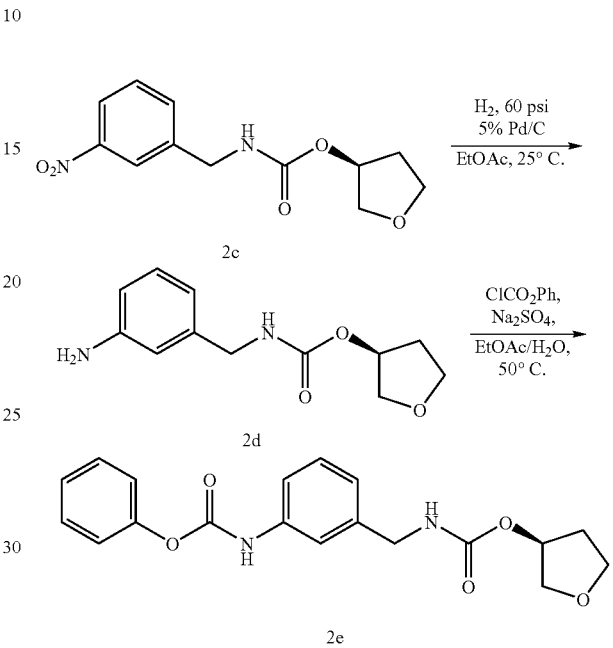

Charged 15 g of (S)-tetrahydrofuran-3-yl 3-nitrobenzylcarbamate 2c in 120 ml EtOAc to a 1L Parr bomb at room temperature under a blanket of N$_2$. The agitator was started and the vessel pressurized with N$_2$ to 0.75 bar, then the pressure was released. This procedure was repeated 3 times, then the agitator was stopped before adding 0.225 g of 5% Pd/C. The agitator was started, the vessel pressurized with N$_2$ to 0.75 bar, then the pressure was released. This procedure was repeated 3 times, then the agitator was stopped. The vessel was pressurized with H$_2$ to 2 bar, then the pressure was released. This procedure was repeated 3 times, then the vessel was pressurized with H$_2$ to 6.75 bar. The agitator was started and the suspension stirred until complete conversion was evident by HPLC. The H$_2$ pressure was released, the vessel re-pressurized with N$_2$ to 0.75 bar, then the pressure was released. This procedure was repeated 3 times then the agitator was stopped, the reaction mixture filtered through celite and the filter cake rinsed with 30 ml EtOAc to give crude (S)-tetrahydrofuran-3-yl 3-aminobenzylcarbamate 2d as a solution in EtOAc that was used as is immediately in the next step.

Dissolved 17.6 g of Na$_2$SO$_4$ in 105 ml water at 20° C. in a separate container. Charged the EtOAc solution of aniline 2d and the aqueous solution of Na$_2$SO$_4$ into a 250 ml glass jacketed vessel purged with N$_2$. The agitator was started to blend the phases and the mixture heated to 50° C. Phenyl chloroformate (7.72 ml) was added dropwise to the solution over 1 hour while maintaining the temperature at 50° C. The reaction was monitored by HPLC for consumption of 2d and phenyl chloroformate. Once the reaction was complete the agitator was stopped, the phases separated and the agitator restarted. Added 60 ml water at 50° C., stirred the contents for 30 minutes at 50° C., then stopped the agitator, separated the layers and restarted the agitator.

The reaction mixture was concentrated to 4 volumes, treated with isopropyl acetate (150 ml), concentrated to 4 volumes, treated with isopropyl acetate (150 ml), concentrated to 4 volumes, then cooled to 15-20° C. and stirred for 30 minutes. The slurry was filtered, then dried under house vacuum at 45° C. until a constant weight to give 17.72 g (88% yield, 99.86% a/a) of {3-[((S)-tetrahydro-furan-3-yloxycarbonylamino)-methyl]-phenyl}-carbamic acid phenyl ester 2e as a colorless crystalline solid with consistent $^1$H NMR (500 MHz, $d_6$-DMSO): 10.20 (br, 1H); 7.85 (br, 1H); 7.40 (m, 4H); 7.25 (t, 2H); 7.20 (d, 1H); 6.95 (m, 1H); 6.75 (m, 1H); 5.15 (m, 1H); 4.15 (d, 2H); 3.75 (m, 2H); 3.70 (m, 2H); 2.10 (m, 1H); 1.90 (m, 1H) ppm.

{3-[((S)-tetrahydro-furan-3-yloxycarbonylamino)-methyl]-phenyl}-carbamic acid phenyl ester (2e)

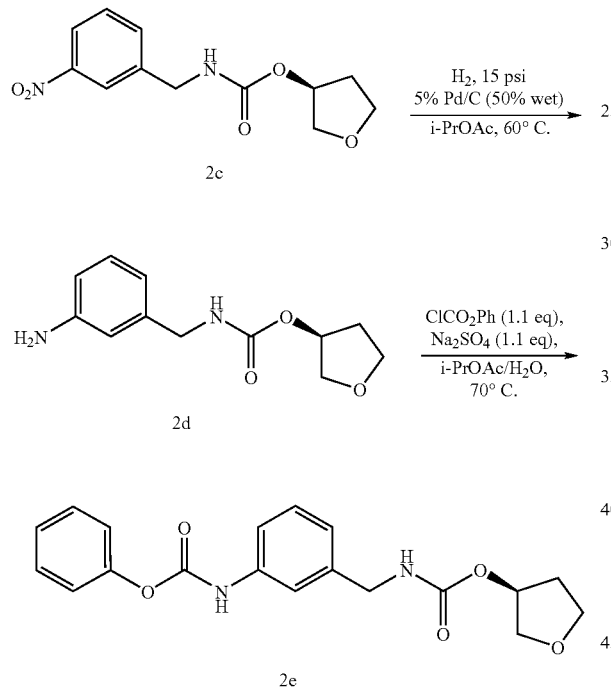

A mixture of 2c (50 g, 1.00 equivalent), 5% Pd/C (0.75 g, 50% water, 0.75 wt %) and isopropyl acetate (400 ml, 8 volumes) was added to a hydrogenation vessel under nitrogen and heated to 60° C. The vessel was pressurized with hydrogen (1.00 bar overpressure) and the mixture stirred at 60° C. The reaction was complete within 3 hours. The pressure was released and the vessel purged with nitrogen. The mixture was filtered through a pad of Celite® and then the hydrogenation vessel and pad were rinsed with isopropyl acetate (100 ml, 2 volumes). The solution of 2d in isopropyl acetate was then combined with a solution of sodium sulfate (29.3 g, 1.10 equivalents) in water (150 ml, 3 vol) and then the mixture was heated to 70° C. Phenyl chloroformate (25.7 ml, 1.10 equivalents) was then added to the mixture while maintaining a temp. of 70° C. The reaction was stirred for 30 min after the end of addition and then the stirring was stopped. The phases were allowed to separate and the aqueous phase was removed. Water (150 ml, 3 vol) was then added and the mixture stirred for an additional 30 min before the stirring was stopped. The phases were allowed to separate and the aqueous phase removed. The mixture was then distilled at atmospheric pressure to azeotropically remove water from the organic phase. Compound 2e precipitated from solution when all of the water was removed. Distillation continued until there were 4 volumes of solvent remaining. The mixture was cooled to 20° C. over 5 hours then filtered to isolate the solid. The reactor and filter cake were washed with isopropyl acetate (2 vol) then the cake was dried under vacuum at 50° C. to afford 61.1 g (91%) of 2e.

3-methoxy-4-(oxazol-5-yl)benzenamine (2g)

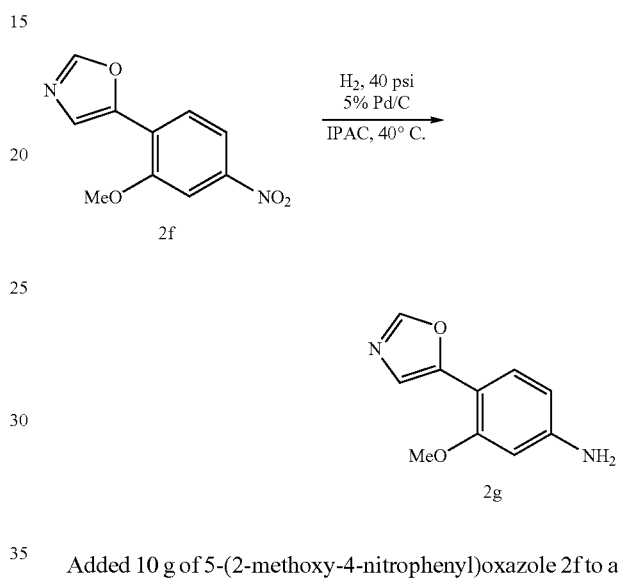

Added 10 g of 5-(2-methoxy-4-nitrophenyl)oxazole 2f to a 500 ml 3-neck flask then added 1.0 g of Nuchar SA.20 charcoal. Next added 200 ml of isopropyl acetate, heated the reaction vessel to 40° C. under nitrogen, stirred for 2 hours at 40° C. then heated to 80° C. and hot filtered to remove the charcoal. The filtrate was concentrated to ½ volume on a rotary evaporator before adding the solution to a 500 ml Parr bomb containing 600 mg of 5% Pd/C (50% wet). The suspension was purged with nitrogen for 20 minutes, then the system was sealed the agitator started. The mixture was heated to 40° C. while continuing the flow of nitrogen, then the bomb was pressurized to 40 psi with hydrogen. The pressure was released, then the vessel re-pressurized with Hydrogen to 40 psi and the process repeated 3 more times. Finally, 40 psi of hydrogen was maintained until intermediate pressure chromatography showed a complete conversion to 3-methoxy-4-(oxazol-5-yl)benzenamine 2g.

Nitrogen was passed through the reaction, the mixture was cooled to room temperature, filtered through Celite, rinsed with 20 ml of isopropyl acetate, then the filtrate volume reduced to ⅓ volume on a rotary evaporator under reduced pressure at 47° C. The mixture was cooled to room temperature, charged with 100 ml n-Heptane, the filtrate volume reduced to ⅓ on a rotary evaporator under reduced pressure at 47° C. and this process was repeated one more time. The mixture was cooled to room temperature, filtered and dried at 45° C. in a house vacuum oven to give 7.91 g of 3-methoxy-4-(oxazol-5-yl)benzenamine 2g (91% yield, 99.7% a/a) as a yellow solid with consistent $^1$H NMR (500 MHz, d6-DMSO): 8.20 (s, 1H); 7.32 (d, 1H); 7.15 (s, 1H); 6.31 (s, 1H); 6.25 (d, 1H); 5.50 (s, 2H); 3.80 (s, 3H) ppm.

3-methoxy-4-(oxazol-5-yl)benzenamine (2g)

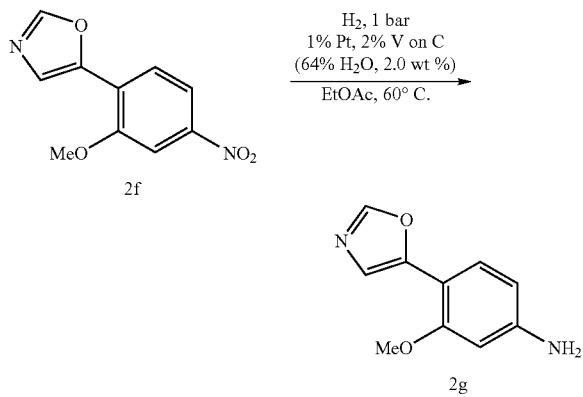

Compound 2f (50 g, 1.0 eq., Nippon Soda) and 1% Pt, 2% V on C (2.78 g, 64% wet, 2.0 wt % on a dry basis, Degussa Type CF1082) were charged to a hydrogenation vessel under nitrogen. Ethyl acetate (500 ml, 10 vol) was added and the mixture was heated to 60° C. The vessel was pressurized with hydrogen (1.00 bar overpressure) and the mixture was stirred at 60° C. The reaction was complete within 3 hours. The pressure was released and nitrogen was bubbled through the reaction mixture. The reaction mixture was filtered through Celite® and washed with EtOAc (100 ml, 2 vol). The solvent level was reduced to 4 vol by distillation at reduced pressure and toluene (500 ml, 10 vol) was charged into the vessel. The solvent level was reduced to 4 vol by distillation at reduced pressure and a second portion of toluene (500 ml, 10 vol) was charged into the vessel. The solvent level was reduced to 5 vol under reduced pressure then the mixture was heated to 90° C. at atmospheric pressure to dissolve any solids. The solution was then cooled slowly to 20° C. to induce crystallization. The resulting yellow solid was filtered and washed with toluene (100 ml, 2 vol) to give compound 2g which was dried in a vacuum oven at 50° C. with a nitrogen bleed until a constant weight of 39.4 g (91%) was achieved.

(S)-tetrahydrofuran-3-yl 3-(3-(3-methoxy-4-(oxazol-5-yl)phenyl)ureido)benzylcarbamate (2h)

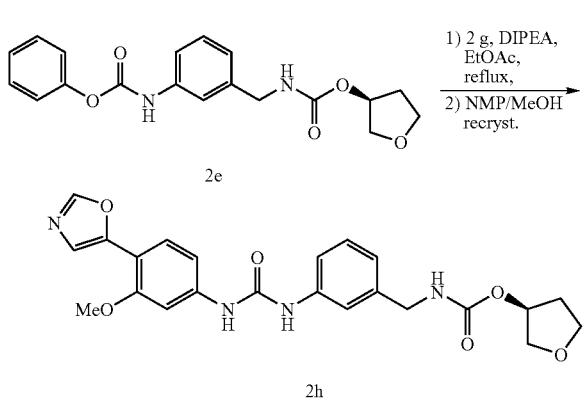

Added 15 g of {3-[((S)-tetrahydro-furan-3-yloxycarbonylamino)-methyl]-phenyl}-carbamic acid phenyl ester 2e and 8.58 g of 3-methoxy-4-(oxazol-5-yl)benzenamine 2g into a 500 ml 3-necked flask and then purged the system with nitrogen before adding 225 ml of ethyl acetate. Next added 5.43 g of diisopropylethylamine over 1 minute, then heated at reflux for 24 hours. Once the reaction was complete, the mixture was cooled to room temperature and stirred for an additional 1 hour. Precipitated solid was filtered, washed with 45 ml of EtOAc 2 times, then dried at 58° C. for 18 hours (until a LOD is achieved of less than 1%) to give 17.46 g of crude (S)-tetrahydrofuran-3-yl 3-(3-(3-methoxy-4-(oxazol-5-yl)phenyl)ureido)benzylcarbamate 2h (90.4% yield, 98.46% a/a) as a white crystalline solid.

Crude 2h was recrystallized in a 500 ml 3-neck flask by the following procedure. 15 g of 2h was dissolved in 84 ml of NMP and stirred for 10 minutes at 20° C. The mixture was heated to 48° C., then MeOH (67.5 ml) was added dropwise over 20 minutes using a syringe pump and the mixture seeded with 0.15 g of crude 2h. The mixture was stirred at 48° C. for 10 minutes, during which time a thin slurry results. Additional MeOH (88.5 ml) was added dropwise using a syringe pump over 90 minutes at 48° C. After completed addition, the reactor was cooled to 0° C. over 5 hours and further stirred at 0° C. for 1 hour. The suspension was filtered, washed 2 times with MeOH (150 ml each) wherein each wash was stirred for 1 hour at ambient temperature and then pressed dry using nitrogen. The solid was dried at 50° C. in a house vacuum oven for 5 hours to give 11.7 g of S)-tetrahydrofuran-3-yl 3-(3-(3-methoxy-4-(oxazol-5-yl)phenyl)ureido)benzylcarbamate 2h (78% recovery, 99.93% a/a) as a white crystalline solid with consistent $^1$H NMR (500 MHz, $d_6$-DMSO): 8.90 (br, 1H); 8.75 (br, 1H); 8.35 (s, 1H); 7.75 (t, 1H); 7.60 (d, 1H); 7.50 (d, 1H); 7.41 (s, 1H); 7.38 (m, 1H); 7.33 (m, 1H); 7.25 (t, 1H); 7.05 (d, 1H); 6.85 (d, 1H); 5.15 (m, 1H); 4.15 (d, 2H); 3.90 (s, 3H); 3.77 (m, 2H); 3.70 (m, 2H); 2.10 (m, 1H); 1.90 (m, 1H) ppm.

(S)-tetrahydrofuran-3-yl 3-(3-(3-methoxy-4-(oxazol-5-yl)phenyl)ureido)benzylcarbamate (2h)

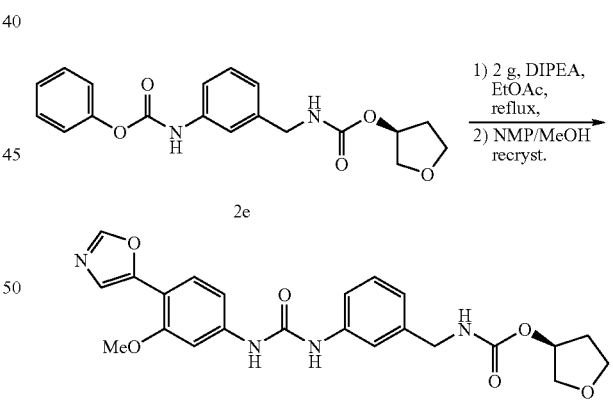

Added 2e (15 g, 1.0 eq) and 2g (8.58 g, 1.07 eq) into a jacketed reactor of suitable size before adding ethyl acetate (225 ml, 15 vol) and diisopropylethylamine (5.43 g, 1.0 eq), then heated the mixture to reflux (75-85° C.) for 24 hours. Once the reaction was complete, the mixture was cooled to room temperature and stirred for an additional 1 hour. Precipitated solid was filtered, washed with EtOAc 2 times (45 ml, 3 vol each wash), then dried at 58° C. for 18 hours (until a LOD is achieved of less than 1%) to give 17.46 g of crude 2h (90.4% yield, 98.46% a/a) as a white crystalline solid.

Crude 2h was recrystallized in a 500 ml 3-neck flask by the following procedure. 15 g of 2h was dissolved in 84 ml of NMP and stirred for 10 minutes at 20° C. The mixture was heated to 48° C., then MeOH (67.5 ml) was added dropwise over 20 minutes using a syringe pump and the mixture seeded with 0.15 g of crude 2h. The mixture was stirred at 48° C. for 10 minutes, during which time a thin slurry results. Additional MeOH (88.5 ml) was added dropwise using a syringe pump over 90 minutes at 48° C. After completed addition, the reactor was cooled to 0° C. over 5 hours and further stirred at 0° C. for 1 hour. The suspension was filtered, washed 2 times with MeOH (150 ml each) wherein each wash was stirred for 1 hour at ambient temperature and then pressed dry using nitrogen. The solid was dried at 50° C. in a house vacuum oven for 5 hours to give 11.7 g of S)-tetrahydrofuran-3-yl 3-(3-(3-methoxy-4-(oxazol-5-yl)phenyl)ureido)benzylcarbamate 2h (78% recovery, 99.93% a/a) as a white crystalline solid with consistent $^1$H NMR (500 MHz, d$_6$-DMSO): 8.90 (br, 1H); 8.75 (br, 1H); 8.35 (s, 1H); 7.75 (t, 1H); 7.60 (d, 1H); 7.50 (d, 1H); 7.41 (s, 1H); 7.38 (m, 1H); 7.33 (m, 1H); 7.25 (t, 1H); 7.05 (d, 1H); 6.85 (d, 1H); 5.15 (m, 1H); 4.15 (d, 2H); 3.90 (s, 3H); 3.77 (m, 2H); 3.70 (m, 2H); 2.10 (m, 1H); 1.90 (m, 1H) ppm.

We claim:

1. A process for preparing a compound of formula II:

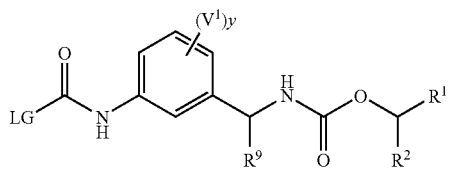

II comprising the steps of:
(a) converting a compound of formula V:

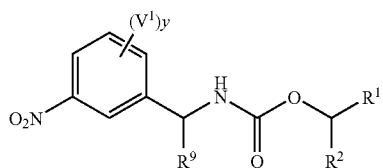

V under suitable catalytic hydrogenation conditions to give a compound of formula IV:

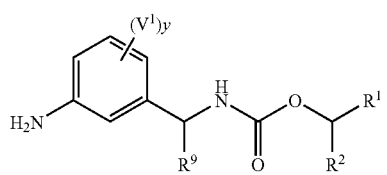

IV or a salt thereof; and
(b) reacting said compound of formula IV with a compound of formula LGC(O)X$^1$, under suitable conditions, wherein:
X$^1$ is a halogen;

LG is —OR$^{16}$; wherein R$^{16}$ is —(C$_1$-C$_6$)-straight or branched alkyl; —(C$_2$-C$_6$)-straight or branched alkenyl or alkynyl; or a monocyclic ring system consisting of 5 to 6 members per ring, wherein said ring system optionally comprises up to 3 heteroatoms selected from N, O, or S, and each R$^{16}$ optionally comprises up to 5 substituents independently selected from (C$_1$-C$_4$)-straight or branched alkyl, (C$_2$-C$_4$) straight or branched alkenyl, or (CH$_2$)—Z;

wherein Z is selected from halogen, CN, NO$_2$, CF$_3$, OCF$_3$, OH, S(C$_1$-C$_4$)-alkyl, SO(C$_1$-C$_4$)-alkyl, SO$_2$(C$_1$-C$_4$)-alkyl, NH$_2$, NH(C$_1$-C$_4$)-alkyl, N((C$_1$-C$_4$)-alkyl)$_2$, COOH, C(O)O(C$_1$-C$_4$)-alkyl or O(C$_1$-C$_4$)-alkyl;

n is 0, 1, 2, 3, or 4;

y is zero;

R$^1$ or R$^2$ is selected from hydrogen, methyl, ethyl or phenyl; and the other of R$^1$ or R$^2$ is selected from —CH$_2$OH, —CH$_2$CN, —CH$_2$CH$_2$CN, or —CH$_2$N(CH$_2$CH$_3$)$_2$; or wherein R$^1$ and R$^2$ are taken together to form a 3-tetrahydrofuranyl moiety;

R$^9$ is hydrogen, (S)-methyl, (S)-ethyl, or (S)-hydroxymethyl;

R$^{10}$ is selected from —C≡N or 5-oxazolyl;

R$^{11}$ is methoxy, ethoxy or isopropoxy;

each V$^1$ is independently selected from halogen, NO$_2$, CN, OR$^{12}$, OC(O)R$^{13}$, OC(O)R$^{12}$, OC(O)OR$^{13}$, OC(O)OR$^{12}$, OC(O)N(R$^{13}$)$_2$, OP(O)(OR$^{13}$)$_2$, SR$^{13}$, SR$^{12}$, S(O)R$^{13}$, S(O)R$^{12}$, SO$_2$R$^{13}$, SO$_2$R$^{12}$, SO$_2$N(R$^{13}$)$_2$, SO$_2$NR$^{12}$R$^{13}$, SO$_3$R$^{13}$, C(O)R$^{12}$, C(O)OR$^{12}$, C(O)R$^{13}$, C(O)OR$^{13}$, NC(O)C(O)R$^{13}$, NC(O)C(O)R$^{12}$, NC(O)C(O)OR$^{13}$, NC(O)C(O)N(R$^{13}$)$_2$, C(O)N(R$^{13}$)$_2$, C(O)N(OR$^{13}$)R$^{13}$, C(O)N(OR$^{13}$)R$^{12}$, C(NOR$^{13}$)R$^{13}$, C(NOR$^{13}$)R$^{12}$, N(R$^{13}$)$_2$, NR$^{13}$C(O)R$^{12}$, NR$^{13}$C(O)R$^{13}$, NR$^{13}$C(O)R$^{12}$, NR$^{13}$C(O)OR$^{13}$, NR$^{13}$C(O)OR$^{12}$, NR$^{13}$C(O)N(R$^{13}$)$_2$, NR$^{13}$C(O)NR$^{12}$R$^{13}$, NR$^{13}$SO$_2$R$^{13}$, NR$^{13}$SO$_2$R$^{12}$, NR$^{13}$SO$_2$N(R$^{13}$)$_2$, NR$^{13}$SO$_2$NR$^{12}$R$^{13}$, N(OR$^{13}$)R$^{13}$, N(OR$^{13}$)R$^{12}$, P(O)(OR$^{13}$)N(R$^{13}$)$_2$, and P(O)(OR$^{13}$)$_2$;

wherein each R$^{12}$ is a monocyclic or a bicyclic ring system consisting of 5 to 6 members per ring, wherein said ring system optionally comprises up to 4 heteroatoms selected from N, O, or S, and wherein a CH$_2$ adjacent to said N, O or S may be substituted with C(O); and each R$^{12}$ optionally comprises up to 3 substituents selected from R$^{11}$;

wherein each R$^{13}$ is independently selected from H, (C$_1$-C$_4$)-straight or branched alkyl, or (C$_2$-C$_4$) straight or branched alkenyl; and wherein each R$^{13}$ optionally comprises a substituent that is R$^{14}$;

wherein R$^{14}$ is a monocyclic or a bicyclic ring system consisting of 5 to 6 members per ring, wherein said ring system optionally comprises up to 4 heteroatoms selected from N, O, or S, and wherein a CH$_2$ adjacent to said N, O or S maybe substituted with C(O); and each R$^{14}$ optionally comprises up to 2 substituents independently chosen from H, (C$_1$-C$_4$)-straight or branched alkyl, or (C$_2$-C$_4$) straight or branched alkenyl, 1,2-methylenedioxy, 1,2-ethylenedioxy, or (CH$_2$)$_n$—Z;

wherein Z is selected from halogen, CN, NO$_2$, CF$_3$, OCF$_3$, OH, S(C$_1$-C$_4$)-alkyl, SO(C$_1$-C$_4$)-alkyl, SO$_2$(C$_1$-C$_4$)-alkyl, NH$_2$, NH(C$_1$-C$_4$)-alkyl, N((C$_1$-C$_4$)-alkyl)$_2$, COOH, C(O)O(C$_1$-C$_4$)-alkyl or O(C$_1$-C$_4$)-alkyl; and wherein any carbon atom in any $R^{13}$ is optionally replaced by O, S, SO, $SO_2$, NH, or $N(C_1\text{-}C_4)$-alkyl; and provided that $R^{16}$ is not a halo-substituted $(C_2\text{-}C_3)$-straight alkyl.

2. The process according to claim 1, wherein:
in step (a) said suitable hydrogenation conditions comprise one or more of the following: a suitable metal catalyst; a suitable solvent selected from a protic solvent, a polar aprotic solvent, a non-polar aprotic solvent or any mixtures thereof; a suitable reaction atmosphere of hydrogen gas at a suitable pressure; and a suitable reaction temperature; and in step (b) said suitable conditions for reacting said intermediate of formula IV with a compound of formula $LGC(O)X^1$ comprises one or more of the following: a suitable solvent selected from a protic solvent, an aprotic solvent or mixtures thereof; a suitable inorganic or organic base; a suitable reaction atmosphere; and a suitable reaction temperature.

3. The process according to claim 2, wherein said process comprises one or more of the following:
in step (a) said metal catalyst is between about 1% to about 30% by weight palladium metal on carbon; said protic solvent is selected from a $(C_1\text{-}C_5)$-straight or branched alkyl alcohol; said aprotic solvent is selected from an ester-type solvent; said reaction atmosphere comprises hydrogen gas at between about one to about ten atmospheres of pressure; and said reaction temperature is between about 20° C. to about 60° C.; and in step (b) said suitable solvent is a mixture of water and an aprotic solvent selected from ethyl acetate, isopropyl acetate, n-butyl acetate, benzene, toluene, xylene, dichloromethane, dichloroethane, chloroform, trifluorotoluene, ethyl ether, isopropyl ether, or methyl t-butyl ether; said reaction atmosphere is selected from air, nitrogen or argon; and said reaction temperature is between about 20° C. and about 80° C.

4. The process according to claim 3, wherein said process comprises one or more of the following:
(a) said metal catalyst is between about 5% to about 10% by weight palladium metal on carbon;
said protic solvent is selected from methanol, ethanol, or isopropanol; said aprotic solvent is selected from ethyl acetate or isopropyl acetate; said reaction atmosphere of hydrogen gas is between about one to about eight atmospheres of pressure; and said reaction temperature is between about 20° C. to about 40° C.; and
(b) said suitable solvent is a mixture of water and an aprotic solvent selected from ethyl acetate or isopropyl acetate; said reaction atmosphere is selected from nitrogen or argon; said inorganic base is selected from $Na_2SO_4$; and said reaction temperature is between about 40° C. and about 60° C.

5. The process according to claim 4, wherein:
(a) said metal catalyst is about 5% by weight palladium metal on carbon; said aprotic solvent is ethyl acetate; said reaction atmosphere of hydrogen gas is between about four and eight atmospheres of pressure; and said reaction temperature is between about 20° C. to about 30° C.; and
(b) said suitable solvent is a mixture of water and an aprotic solvent selected from ethyl acetate or isopropyl acetate; said reaction atmosphere is selected from nitrogen; said reaction temperature is between about 40° C. and about 60° C.

6. The process according to claim 1, wherein:
$R^{16}$ is a monocyclic ring system consisting of 6 members per ring, wherein said ring system optionally comprises up to 2 heteroatoms selected from N, O, or S, and each $R^{16}$ optionally comprises up to 5 substituents independently selected from $(C_1\text{-}C_4)$-straight or branched alkyl, or $(CH_2)_n$—Z.

7. The process according to claim 6, wherein:
$R^{16}$ is a phenyl ring optionally comprising up to 5 substituents independently selected from $(C_1\text{-}C_4)$-straight or branched alkyl, or $(CH_2)_n$—Z.

8. The process according to claim 7, wherein $R^{16}$ is a phenyl ring.

9. The process according to claim 1, wherein:
$R^1$ and $R^2$ are taken together to form a 3-tetrahydrofuranyl ring; and
$R^9$ is hydrogen.

10. The process according to claim 1, wherein:
$R^1$ or $R^2$ is ethyl; and the other of $R^1$ or $R^2$ is —$CH_2CN$; and
$R^9$ is (S)-methyl.

11. The process according to claim 1, wherein said compound of formula V:

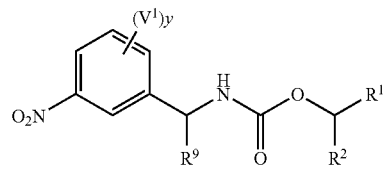

is prepared by a process comprising the steps of:
(a) reacting a compound of formula VII with a phosgene reagent or a suitable phosgene reagent equivalent, under suitable conditions, to prepare a compound of formula VIII;

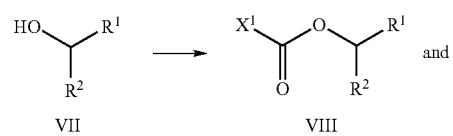

(b) reacting said compound of formula VIII, or a synthetically acceptable analog or derivative thereof, with a compound of formula IX, or a synthetically acceptable analog or derivative thereof, under suitable conditions:

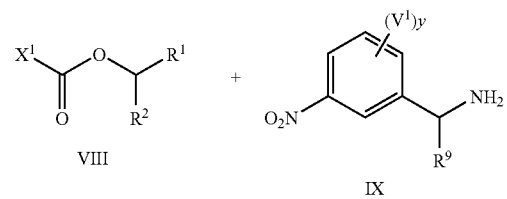

wherein:
$X^1$ is halogen;
y is zero;
$R^1$ or $R^2$ is selected from hydrogen, methyl, ethyl or phenyl; and the other of $R^1$ or $R^2$ is selected from —$CH_2OH$, —$CH_2CN$, —$CH_2CH_2CN$, or —$CH_2N(CH_2CH_3)_2$; or wherein $R^1$ and $R^2$ are taken together to form a 3-tetrahydrofuranyl moiety;

$R^9$ is hydrogen, (S)-methyl, (S)-ethyl, or (S)-hydroxymethyl;

each $V^1$ is independently selected from halogen, $NO_2$, CN, $OR^{12}$, $OC(O)R^{13}$, $OC(O)R^{12}$, $OC(O)OR^{13}$, $OC(O)OR^{12}$, $OC(O)N(R^{13})_2$, $OP(O)(OR^{13})_2$, $SR^{13}$, $SR^{12}$, $S(O)R^{13}$, $S(O)R^{12}$, $SO_2R^{13}$, $SO_2R^{12}$, $SO_2N(R^{13})_2$, $SO_2NR^{12}R^{13}$, $SO_3R^{13}$, $C(O)R^{12}$, $C(O)OR^{12}$, $C(O)R^{13}$, $C(O)OR^{13}$, $NC(O)C(O)R^{13}$, $NC(O)C(O)R^{12}$, $NC(O)C(O)OR^{13}$, $NC(O)C(O)N(R^{13})_2$, $C(O)N(R^{13})_2$, $C(O)N(OR^{13})R^{13}$, $C(O)N(OR^{13})R^{12}$, $C(NOR^{13})R^{13}$, $C(NOR^{13})R^{12}$, $N(R^{13})_2$, $NR^{13}C(O)R^{12}$, $NR^{13}C(O)R^{13}$, $NR^{13}C(O)R^{12}$, $NR^{13}C(O)OR^{13}$, $NR^{13}C(O)OR^{12}$, $NR^{13}C(O)N(R^{13})_2$, $NR^{13}C(O)NR^{12}R^{13}$, $NR^{13}SO_2R^{13}$, $NR^{13}SO_2R^{12}$, $NR^{13}SO_2N(R^{13})_2$, $NR^{13}SO_2NR^{12}R^{13}$, $N(OR^{13})R^{13}$, $N(OR^{13})R^{12}$, $P(O)(OR^{13})N(R^{13})_2$, and $P(O)(OR^{13})_2$;

wherein each $R^{12}$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S may be substituted with C(O); and each $R^{12}$ optionally comprises up to 3 substituents selected from $R^{11}$;

wherein each $R^{13}$ is independently selected from H, ($C_1$-$C_4$)-straight or branched alkyl, or ($C_2$-$C_4$) straight or branched alkenyl; and wherein each $R^{13}$ optionally comprises a substituent that is $R^{14}$;

wherein $R^{14}$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S maybe substituted with C(O); and each $R^{14}$ optionally comprises up to 2 substituents independently chosen from H, ($C_1$-$C_4$)-straight or branched alkyl, or ($C_2$-$C_4$) straight or branched alkenyl, 1,2-methylenedioxy, 1,2-ethylenedioxy, or $(CH_2)_n$—Z;

wherein Z is selected from halogen, CN, $NO_2$, $CF_3$, $OCF_3$, OH, S($C_1$-$C_4$)-alkyl, SO($C_1$-$C_4$)-alkyl, $SO_2$($C_1$-$C_4$)-alkyl, $NH_2$, NH($C_1$-$C_4$)-alkyl, N(($C_1$-$C_4$)-alkyl)$_2$, N(($C_1$-$C_4$)-alkyl)$R^{15}$, COOH, C(O)O($C_1$-$C_4$)-alkyl or O($C_1$-$C_4$)-alkyl;

wherein n is 0, 1, 2, 3, or 4; and wherein $R^{15}$ is an amino protecting group; and wherein any carbon atom in any $R^{13}$ is optionally replaced by O, S, SO, $SO_2$, NH, or N($C_1$-$C_4$)-alkyl.

12. The process according to claim 11, wherein said process comprises one or more of the following:

in step (a) said phosgene reagent is about a 10% to about a 30% solution of phosgene in toluene; said suitable conditions comprise a suitable solvent selected from a nonpolar aprotic solvent; a suitable organic base; a suitable reaction atmosphere; a suitable reaction temperature; and a suitable reaction time; and in step (b) said suitable conditions comprise a suitable solvent selected from a protic solvent, an aprotic solvent, or mixtures thereof; a suitable inorganic or organic base; a suitable reaction atmosphere; a suitable reaction temperature; and a suitable reaction time.

13. The process according to claim 12, wherein said process comprises one or more of the following:

in step (a) said phosgene reagent is about a 20% solution of phosgene in toluene; said nonpolar aprotic solvent is benzene or toluene; said organic base is pyridine; said suitable reaction atmosphere is nitrogen or argon; said suitable reaction temperature is between about 20° C. and about 60° C.; and said suitable reaction time is between about 1 hour to about 48 hours;

in step (b) said suitable conditions comprise a suitable solvent mixture; a suitable organic base; a suitable reaction atmosphere; a suitable reaction temperature; and a suitable reaction time; and said suitable solvent mixture comprises a mixture of a protic solvent and an aprotic solvent wherein said protic solvent is water, and wherein said aprotic solvent is selected ethyl acetate, isopropyl acetate, n-butyl acetate, benzene, toluene, xylene, dichloromethane, dichloroethane, chloroform, trifluorotoluene, ethyl ether, isopropyl ether, or methyl t-butyl ether; said inorganic base is selected from $Na_2CO_3$, $K_2CO_3$, $Cs_2CO_3$, $Li_2CO_3$, $NaHCO_3$, $KHCO_3$, NaOH, KOH, LiOH; said reaction atmosphere is selected from air, nitrogen or argon; said reaction temperature is between about 20° C. and about 80° C.; and said reaction time is between about 30 minutes to about 24 hours.

14. The process according to claim 11, wherein:
$X^1$ is chlorine.

15. The process according to claim 11, wherein:
y is zero;
$R^1$ and $R^2$ are taken together to form a 3-tetrahydrofuranyl moiety; and
$R^9$ is hydrogen, or (S)-methyl.

16. The process according to claim 11, wherein:
$R^1$ or $R^2$ is selected from hydrogen, methyl, ethyl or phenyl; and the other of $R^1$ or $R^2$ is selected from —$CH_2OH$, —$CH_2CN$, —$CH_2CH_2CN$, or $CH_2N(CH_2CH_3)_2$; and
$R^9$ is hydrogen or (S)-methyl.

* * * * *